(12) United States Patent
Howard

(10) Patent No.: US 9,512,098 B1
(45) Date of Patent: Dec. 6, 2016

(54) PROCESS OF PRODUCING PURIFIED GAMMA- AND DELTA-TOCOTRIENOLS FROM TOCOL-RICH OILS OR DISTILLATES

(71) Applicant: Board of Trustees of the University of Arkansas, Little Rock, AR (US)

(72) Inventor: Luke Howard, West Fork, AR (US)

(73) Assignee: Board of Trustees of the University of Arkansas, Little Rock, AR (US)

(*) Notice: Subject to any disclaimer, the term of this patent is extended or adjusted under 35 U.S.C. 154(b) by 0 days.

(21) Appl. No.: 14/611,677

(22) Filed: Feb. 2, 2015

Related U.S. Application Data

(60) Provisional application No. 61/935,065, filed on Feb. 3, 2014.

(51) Int. Cl.
*C07D 311/72* (2006.01)

(52) U.S. Cl.
CPC .................. *C07D 311/72* (2013.01)

(58) Field of Classification Search
CPC .................................................. C07D 311/72
See application file for complete search history.

(56) References Cited

U.S. PATENT DOCUMENTS

| | | |
|---|---|---|
| 4,603,142 A | 7/1986 | Burger et al. |
| 5,190,618 A | 3/1993 | Top et al. |
| 5,217,992 A | 6/1993 | Wright et al. |
| 5,348,974 A | 9/1994 | Wright et al. |
| 5,591,772 A | 1/1997 | Lane et al. |
| 5,821,264 A | 10/1998 | Lane et al. |
| 5,908,940 A | 6/1999 | Lane et al. |
| 5,919,818 A | 7/1999 | Lane et al. |
| 5,985,344 A | 11/1999 | Cherukuri et al. |
| 6,063,424 A | 5/2000 | Wells et al. |
| 6,143,770 A | 11/2000 | Lane et al. |
| 6,187,811 B1 | 2/2001 | Lane |
| 6,204,290 B1 | 3/2001 | Lane et al. |
| 6,224,717 B1 | 5/2001 | Sumner, Jr. et al. |
| 6,239,171 B1 | 5/2001 | Lane et al. |
| 6,350,473 B1 | 2/2002 | Cheruvanky et al. |

(Continued)

FOREIGN PATENT DOCUMENTS

| | | |
|---|---|---|
| JP | 6193178 | 5/1986 |
| WO | 2005032478 | 4/2005 |
| WO | 2014100327 | 6/2014 |

OTHER PUBLICATIONS

Cooper, W.T., "Normal-Phase Liquid Chromatography." Encyclopedia of Analytical Chemistry, John Wiley & Sons, 2006, p. 1-15.*

(Continued)

*Primary Examiner* — Samantha Shterengarts
*Assistant Examiner* — Matt Mauro
(74) *Attorney, Agent, or Firm* — Crowe & Dunlevy, P.C.

(57) ABSTRACT

The invention is generally directed to a process of producing purified gamma- and/or delta-tocotrienols from tocol-rich oils or distillates, such as rice bran oil deodorizer distillate or palm oil. The process produces a gamma- and/or delta-tocotrienol-rich fraction in a high proportion of γ-T3 and/or δ-T3 while minimizing the presence of alpha isomers from the tocol-rich oil or distillate. The γ-T3- and/or δ-T3-rich fraction comprises about 95% of total tocols, with the process yielding γ-T3 in approximately 10% and δ-T3 in about 3%, with each having purity in excess of approximately 95%. The process utilizes flash or other low pressure chromatography to provide rapid isolation of gamma- and/or delta-tocotrienol from the tocol-rich oil or distillate.

23 Claims, 19 Drawing Sheets

(56) References Cited

U.S. PATENT DOCUMENTS

| | | | |
|---|---|---|---|
| 6,395,915 | B1 | 5/2002 | Bellafiore et al. |
| 6,558,714 | B2 | 5/2003 | Cheruvanky et al. |
| 6,656,358 | B2 | 12/2003 | May et al. |
| 6,716,873 | B1 | 4/2004 | Keramidas et al. |
| 6,733,799 | B2 | 5/2004 | Cheruvanky et al. |
| 7,038,067 | B2 | 5/2006 | Couladouros et al. |
| 7,790,190 | B2 | 9/2010 | Papas et al. |
| 7,919,525 | B2 | 4/2011 | Kumar et al. |
| 8,106,223 | B2 | 1/2012 | Wesson et al. |
| 2004/0026323 | A1 | 2/2004 | Kaneko et al. |
| 2005/0074445 | A1 | 4/2005 | Papas et al. |
| 2005/0209315 | A1 | 9/2005 | Papas et al. |
| 2011/0196030 | A1* | 8/2011 | El Sayed et al. ............ 514/458 |

OTHER PUBLICATIONS

Claeson, P., F.,"Some empirical aspects on the practical use of flash chromatography and medium pressure liquid chromatography for the isolation of biologically active compounds from plants." Journal of the Scientific Society of Thailand 19 (1993): 73-86.*
Stevens, W.C.,"General methods for flash chromatography using disposable columns." Molecular diversity 13.2 (2009): 247-252.*
Maret G. Traber, Jeffrey Atkinson, Vitamin E, antioxidant and nothing more, Free Radical Biology & Medicine 43 (2007) 4-15.
Xiang Hong Li, Dadin Fu, Nabil H. Latif, Conor P. Mullaney, Patrick H. Ney, Steven R. Mog, Mark H. Whitnall, Venkataraman Srinivasan, and Mang Xiao, d-tocotrienol protects mouse and human hematopoietic progenitors from g-irradiation through extracellular signal-regulated kinase/mammalian target of rapamycin signaling, Haematologica 2010;95(12):1996-2004. doi:10.3324/haematol.2010.026492.
Ko S-N, Lee S-M, Kim I-H. 2008. The concentration of tocols from rice bran oil deodorizer distillate using solvent. Eur J Lipid Sci Technol 110:914-919.
Lim H, Woo S, Kim HS, Jong S-K, Lee J. 2007. Comparison of extraction methods for determining tocopherols in soybeans. Eur J Lipid Sci Technol 109:1124-1127.
Qureshi AA, Burger WC, Peterson DM, Elson CE. 1986. The structure of an inhibitor of cholesterol biosynthesis isolated from barley. J Biol Chem 261(3):10544-10550.
Qureshi AA, Mo H, Packer L, Peterson DM. 2000a. Isolation and identification of novel tocotrienols from rice bran with hypocholesterolemic, antioxidant, and antitumor properties. J Agric Food Chem 48:3130-3140.
Qureshi AA, Pearce BC, Nor RM, Gapor A, Peterson DM, Elson CE. 1996. Dietary α-tocopherol attenuates the impact of γ-tocotrienol on hepatic 3-hydroxy-3-methylglutaryl coenzyme A reductase activity in chickens. J Nutr 126 (2):389-394.
Qureshi AA, Peterson DM. 2001. The combined effects of novel tocotrienols and lovastatin on lipid metabolism in chickens. Atherosclerosis 156:39-47.
Qureshi AA, Peterson DM, Hasler-Rapacz JO, Rapacz J. 2000b. Novel tocotrienols of rice bran suppress cholesterogenesis in hereditary hypercholesterolemic swine. J Nutr 131(2):223-230.
Qureshi AA, Qureshi N, Wright JJK, Shen Z, Kramer G, Gapor A, Chong YH, DeWitt G, Ong ASH, Peterson DM, Bradlow BA. 1991. Lowering of serum cholesterol in hypercholesterolemic humans by tocotrienols (palmvitee). Am J Clin Nutr 53:10215-10265.
Qureshi AA, Sami SA, Khan FA. 2001a. Effects of stabilized rice bran, its soluble and fiber fractions on blood glucose levels and serum lipid parameters in humans with diabetes mellitus Types I and II. J Nutr Biochem 13:175-187.
Qureshi AA, Sami SA, Salser WA, Khan FA. 2001b. Synergistic effect of tocotrienol-rich fraction (TRF25) of rice bran and lovastatin on lipid parameters in hypercholesterolemic humans. J Nutr Biochem 12:318-329.
Qureshi AA, Sami SA, Salser WA, Khan FA. 2002. Dose-dependent suppression of serum cholesterol by tocotrienol-rich fraction (TRF25) of rice bran in hypercholesterolemic humans. Atherosclerosis 161(1):199-207.
Rawlings HW. 1944. The chemical determination of tocopherols in distilled concentrates. J Am Oil Chem Soc 21:257-257.
Ryynänen M, Lampi A-M, Salo-Väänänen P, Ollilainen V, Piironen,V. 2004. A small-scale sample preparation method with HPLC analysis for determination of tocopherols and tocotrienols in cereals. J Food Comp Anal 17:749-765.
Shimada Y, Nakai S, Suenaga M, Sugihara A, Kitano M, Tominaga Y. 2000. Facile purification of tocopherols from soybean oil deodorizer distillate in high yield using lipase. J Am Oil Chem Soc 77(10):1009-1013.
Shin T-S, Godber JS. 1994. Isolation of four tocopherols and four tocotrienols from a variety of natural sources by semi-preparative high-performance liquid chromatography. J Chromatography A 678:49-58.
Mary Kordsmeier, Extraction and Purification of Gamma-Tocotrienol from Rice Bran Oil Deodorizer Distillate, Thesis, May 2013, University of Arkansas.
Teledyne Isco, Inc. n.d. Chromatography Application Note AN27. Available from: http://www.isco.com/WebProductFiles/Applications/101/Application_Notes/AN27_Rapid_Purification_of_Tocopherols.pdf. Accessed Mar. 1, 2013.
Torres, Cf, Torello, G, Reglero, G. 2011. Extraction and enzymatic modification of functional lipids from soybean oil deodorizer distillate, Recent Trends for Enhancing the Diversity and Quality of Soybean Products, Krezhova, D (ed), InTech, available from: http://www.intechopen.com/books/recent-trends-for-enhancing-the-diversity-and-quality-of-soybean-products/extraction-and-enzymatic-modification-of-functional-lipids-from-soybean-oil-deodorizer-distillate.
Wan J, Zhang W, Jiang B, Guo Y, Hu C. 2008. Separation of individual tocopherols from soybean distillate by low pressure column chromatography. J Am Oil Chem Soc 85:331-338.
Tan B, Watson R, Preedy V, Tocotrienols Vitamin E Beyond Tocopherols, Second Edition, CRC Press, Chap 26.
Sanchita P. Ghosh, Shilpa Kulkarni, Kevin Hieber, Raymond Toles, Lyudmila Romanyukha, Tzu-Cheg Kao, Martin Hauer-Jensen, & K. Sree Kumar, Gamma-tocotrienol, a tocol antioxidant as a potent radioprotector, Int. J. Radiat. Biol., vol. 85, No. 7, Jul. 2009, pp. 598-606.
K. Sree Kumar, Sanchita P. Ghosh and Martin Hauer-Jensen; Gamma-Tocotrienol: Potential as a Countermeasure against Radiological Threat, Tocotrienols Vitamin E Beyond Tocopherols, Second Edition, CRC Press, Chap 27.
Maaike Berbée, Qiang Fu, Marjan Boerma, Junru Wang, K. Sree Kumar, and Martin Hauer-Jensen; γ-Tocotrienol Ameliorates Intestinal Radiation Injury and Reduces Vascular Oxidative Stress after Total-Body Irradiation by an HMG-CoA Reductase-Dependent Mechanism, Radiation Research, 171(5):596-605. 2009.
Sanchita P. Ghosh/ Martin 1-lauer-jensen and K. Sree Kumar, Chemistry of Tocotrienols, ocotrienols Vitamin E Beyond Tocopherols, Second Edition, CRC Press, Chap 7.
Maaike Berbee, M.D., Qiang Fu, M.D., Ph.D., Marjan Boerma, Ph.D., Rupak Pathak, Ph.D., Daohong Zhou, M.D., K. Sree Kumar, Ph.D., and Martin Hauer-Jensen, M.D., Ph.D.*z, Reduction of Radiation-Induced Vascular Nitrosative Stress by He Vitamin E Analog g-Tocotrienol: Evidence of a Role for Tetrahydrobiopterin, Int. J. Radiation Oncology Biol. Phys., vol. 79, No. 3, pp. 884-891, 2011.
Maaike Berbée, Qiang Fu, Sarita Garg, Shilpa Kulkarni, K. Sree Kumar, and Martin Hauer-Jensen, Pentoxifylline Enhances the Radioprotective Properties of γ-Tocotrienol:Differential Effects on the Hematopoietic, Gastrointestinal and Vascular Systems, Radiation Research, 175(3):297-306.2011.
Shilpa Kulkarni,1 Kushal Chakraborty,1 K. Sree Kumar,1 Tzu-Cheg Kao,1 Martin Hauer-Jensen,2 and Sanchita P. Ghosh, Synergistic Radioprotection by Gamma-Tocotrienol and Pentoxifylline: Role of cAMP Signaling, Hindawi Publishing Corporation, ISRN Radiology, vol. 2013, Article ID 390379, 11 pages.
Shilpa Kulkarni,a,1,2 Sanchita P. Ghosh,a,2 Merriline Satyamitra,a,2 Steven Mog,a Kevin Hieber,a Lyudmila Romanyukha,a Kristen Gambles,a Raymond Toles,a Tzu-Cheg Kao,a Martin Hauer-Jensenb and K. Sree Kumara, Gamma-

(56) References Cited

OTHER PUBLICATIONS

Tocotrienol Protects Hematopoietic Stem and Progenitor Cells in Mice after Total-Body Irradiation, Radiation Research 173,738-747 (2010).

Shilpa S. Kulkarni a, Lynnette H. Cary a, Kristen Gambles a, Martin Hauer-Jensen b, K. Sree Kumar a, Sanchita P. Ghosh, Gamma-tocotrienol, a radiation prophylaxis agent, induces high levels of granulocyte colony-stimulating factor, International Immunopharmacology 14 (2012) 495-503.

Grazyna Nowak, Diana Bakajsova, Corey Hayes, Martin Hauer-Jensen, and Cesar M. Compadre, γ-Tocotrienol Protects against Mitochondrial Dysfunction and Renal Cell Death, The Journal of Pharmacology and Experimental Therapeutics, vol. 340, No. 2,186882/3742099.

Sugata Ray a,1, Shilpa S. Kulkarni a,1, Kushal Chakraborty a,1, Roli Pessu a, Martin Hauer-Jensen b, K. Sree Kumar a, Sanchita P. Ghosh, Mobilization of progenitor cells into peripheral blood by gamma-tocotrienol: A promising radiation countermeasure, International Immunopharmacology 15 (2013) 557-564.

Maaike Berbe'e • Qiang Fu • Marjan Boerma, K. Sree Kumar • David S. Loose • Martin Hauer-Jensen, Mechanisms underlying the radioprotective properties of c-tocotrienol: comparative gene expression profiling in tocol-treated endothelial cells, Genes Nutr (2012) 7:75-81, DOI 10.1007/s12263-011-0228-8.

Orthoefoer, Frank, Rice Bran Oil, 2005.

Tai-Sun Shin, J. Samuel Godber*; Isolation of four tocopherols and four tocotrienols from a variety of natural sources by semi-preparative high performance liquid chromatography*, Journal of Chromatography A, 678 (1994) 49-58.

Kumuthini Chandrasekaram, Analysis of Phytonutrients From Palm Concentrates by High Performance Liquid Chromatography, Faculty of Science, University of Malaya, Kuala Lumpur, Malaysia, 2009.

* cited by examiner

PROCESS OF PRODUCING PURIFIED GAMMA- AND DELTA-TOCOTRIENOLS FROM TOCOL-RICH OILS OR DISTILLATES

CROSS REFERENCE TO RELATED APPLICATIONS

This application claims the benefit of U.S. Provisional Patent Application Ser. No. 61/935,065, entitled "Process of Purifying Gamma Tocols from Rice Bran Oil Deodorizer Distillate," filed Feb. 3, 2014, which is incorporated herein by reference in its entirety.

STATEMENT REGARDING FEDERALLY SPONSORED RESEARCH OR DEVELOPMENT

Not Applicable.

NAMES OF THE PARTIES TO A JOINT RESEARCH AGREEMENT

Not Applicable.

REFERENCE TO A SEQUENCE LISTING, A TABLE, OR A COMPUTER PROGRAM LISTING APPENDIX

Not Applicable.

STATEMENT REGARDING PRIOR DISCLOSURES BY THE INVENTOR OR A JOINT INVENTOR

Not Applicable.

BACKGROUND OF THE INVENTION

1. Field of the Invention

This invention relates generally to a process of producing purified gamma- and/or delta-tocotrienols from tocol-rich oils or distillates, and more particularly to a process of producing a gamma- and/or delta-tocotrienol-rich fraction or extract from rice bran oil deodorizer distillate, palm oil or other tocol-rich oil or distillate.

2. Description of the Related Art

Rice bran oil (RBO) is generally produced by extracting oil from the heat stabilized rice bran, either by hydraulic pressing or solvent extraction. Crude RBO goes through a series of refining steps, including degumming, neutralization, bleaching, dewaxing, winterization and deodorization. Deodorization employs high heat steam distillation to remove volatile compounds that could give RBO undesirable flavor or odor. Unsaponifiables, such as vitamin E and sterols, are also removed from the oil resulting in deodorizer distillate with a high level of these compounds. Up to 90% of the tocotrienols present in rice bran may be lost to the deodorizer distillate during the refining process.

Additionally, tocotrienol-rich fractions or concentrates have been prepared from palm oil sources. Commercial tocotrienol rich fractions (TRF) isolated from palm oil contain about 20 to 30% tocols of which gamma tocotrienol accounts for about half, and alpha tocopherol accounts for about 20%.

Vitamin E is a family made up of eight major lipid-soluble antioxidants: d-α-tocopherol (α-T), d-β-tocopherol (β-T), d-γ-tocopherol (γ-T), d-δ-tocopherol (δ-T), d-α-tocotrienol (α-T3), d-β-tocotrienol (β-T3), d-γ-tocotrienol (γ-T3) and d-δ-tocotrienol (δ-T3). Tocopherols and tocotrienols, collectively called tocols, have a 6-chromanol ring at the base of their structure with a hydrocarbon chain at the 2-position. The structures of these vitamin E groups differ only in the degree of saturation of their hydrophobic tail, with tocopherols being fully saturated and tocotrienols containing three double bonds. α-, β-, γ- and δ-tocols are characterized by the number and position of methyl substituents on the aromatic ring.

α-T is the only vitamin E compound to meet dietary vitamin E requirements due to its preferential retention in the body by hepatic α-T transfer protein (α-TTP). All tocols, however, have antioxidant activity and may protect against oxidative stress, which has been linked to many diseases, such as cancer, cardiovascular disease, diabetes, neurodegenerative diseases (e.g., Alzheimer's, Parkinson's), among others. Rice bran (RB) and RBO consumption has been shown to reduce cholesterol in numerous studies in which the hypocholesterolemic ability of RB products is due to the unsaponifiable content, specifically tocotrienols, including γ-T3, and their ability to inhibit HMG-CoA reductase, the rate-limiting enzyme in cholesterol biosynthesis. Tocotrienols have also been shown to have much more potent antiproliferative and apoptotic effects on carcinogenic cells than tocopherols. γ-T3 and δ-T3 are generally considered to be the strongest anti-carcinogenic agents of the tocol family.

In addition, tocols, especially γ-T3, have been shown to have the ability to act as radiation countermeasures, and several studies have been conducted to investigate the degree to which γ-T3 ameliorates radiation injury. Treatment with γ-T3 in irradiated mice resulted in increased survival rates, improved hematopoietic recovery and reduced vascular oxidative stress caused by irradiation. It has also been suggested that δ-T3 may also provide some significant radioprotective potential. Outside of emergency nuclear situations, the radioprotective effects of γ-T3 and δ-T3 may be useful in therapy for radiation treatments in cancer patients as well; however, co-administration of α-T has been shown to cause interference with the hypocholesterolemic and anti-carcinogenic effects of γ-T3 and δ-T3, and may adversely affect the radioprotective properties of γ-T3.

Several methods have been proposed to recover tocols from vegetable oil refining by-products including; distillation, supercritical carbon dioxide, and solvent fractionation in combination with a cold crystallization step, but these methods do not result in satisfactory isolation/purification of individual tocols including gamma or delta-tocotrienol. Flash chromatography has been used for fractionation of mixtures, employing short columns packed with intermediate size particles (40-60 μm) with accelerated solvent flow achieved by modest pressure. Flash chromatography has been used to isolate a tocol rich fraction from rice bran, with diethyl ether as elution solvent, but the usage of ether poses serious safety hazards. Others have used a diol column and a linear gradient of increasing isopropanol in hexane to purify tocopherols from corn and soybean oils. Yet another method for separating tocotrienols from a tocol-containing mixture involves a combination of heating, distillation, and series of solvent partitioning steps, but the method does not result in high purity of gamma-tocotrienol. None of these prior methods, however, separate individual tocols, including gamma- and/or delta-tocotrienol.

It is therefore desirable to provide a process of producing purified gamma- and delta-tocotrienols from tocol-rich oils or distillates.

It is further desirable to provide a process of producing a gamma- and/or delta-tocotrienol-rich fraction from tocol-rich oils or distillates that results in a high proportion of γ-T3 and/or δ-T3 while minimizing the presence of alpha isomers from the tocol-rich oils or distillates.

It is yet further desirable to provide a process of producing purified γ-T3 and/or δ-T3 from tocol-rich oils or distillates that does not use toxic solvents, such as ether, and that uses much less organic solvent than semi-preparative HPLC, resulting in a cheaper and more environmentally friendly process.

It is still further desirable to provide a process of producing a γ-T3 and/or δ-T3-rich fraction from tocol-rich oils or distillates where gamma- and/or delta-tocotrienol comprises about 95% of total tocols, with a gamma-tocotrienol yield of approximately 10% and/or a delta-tocotrienol yield of about 3%, and with purity in excess of about 95%.

It is further desirable to provide a process of producing a gamma- and/or delta-tocotrienol-rich fraction from tocol-rich oils or distillates using a fast flash or low pressure liquid chromatography.

It is further desirable to provide a γ-T3- and/or δ-T3-rich extract for use as an antioxidant ingredient in lipid-containing foods (e.g., pet foods), cosmetics, personal care products, vitamin supplements, pharmaceuticals and/or nutraceuticals.

It is further desirable to provide a γ-T3- and/or δ-T3-rich extract that can be incorporated into a highly purified γ-T3- and/or δ-T3-tocotrienol or a γ-T3- and/or δ-T3-tocotrienol-rich product for use in the medical field as a radio-protective compound, i.e., given to cancer patients undergoing radiation treatment, sold as a dietary supplement, and/or used by individuals exposed to radiation poisoning as a result of a nuclear accident or terrorist activity.

Other advantages and features of the invention will be apparent from the following description and from the claims.

BRIEF SUMMARY OF THE INVENTION

In general, in a first aspect, the invention relates to a process of producing gamma- and/or delta-tocols from a tocol-rich oil. In this aspect, the process includes distilling the tocol-rich oil to produce a tocol concentrate, and then purifying the tocol concentrate using low pressure chromatography to produce a gamma and/or delta tocotrienol-rich fraction.

In general, in a second aspect, the invention relates to a process of producing a d-γ-tocotrienol and/or δ-tocotrienol extract from a tocol-rich concentrate. In this aspect, the process includes producing the d-γ-tocotrienol and/or δ-tocotrienol extract from the tocol-rich concentrate using low pressure chromatography for a predetermined amount of time.

According to either aspect of the invention, the low pressure chromatography may be flash or low pressure liquid chromatography, and more particularly may be flash chromatography with a binary gradient comprising hexane-acetic acid and ethyl acetate-acetic acid for between about 50 minutes and about 55 minutes. The gamma- and/or delta-tocotrienol-rich fraction is a d-γ-tocotrienol-rich fraction, a δ-tocotrienol-rich fraction or mixture thereof, and is substantially free from α-tocols. In addition, the gamma- and/or delta-tocotrienol-rich fraction or the d-γ-tocotrienol and/or δ-tocotrienol extract include about 95% total tocols, with a gamma-rich yield of about 10% and a delta-rich yield of about 3%, each having purity in excess of approximately 95%. Moreover, the tocol concentrate contains between about 20% and 50% total tocols, and may be obtained by distillation of a tocol-rich oil, such as rice bran oil or palm oil.

DETAILED DESCRIPTION OF THE INVENTION

Figure 1:
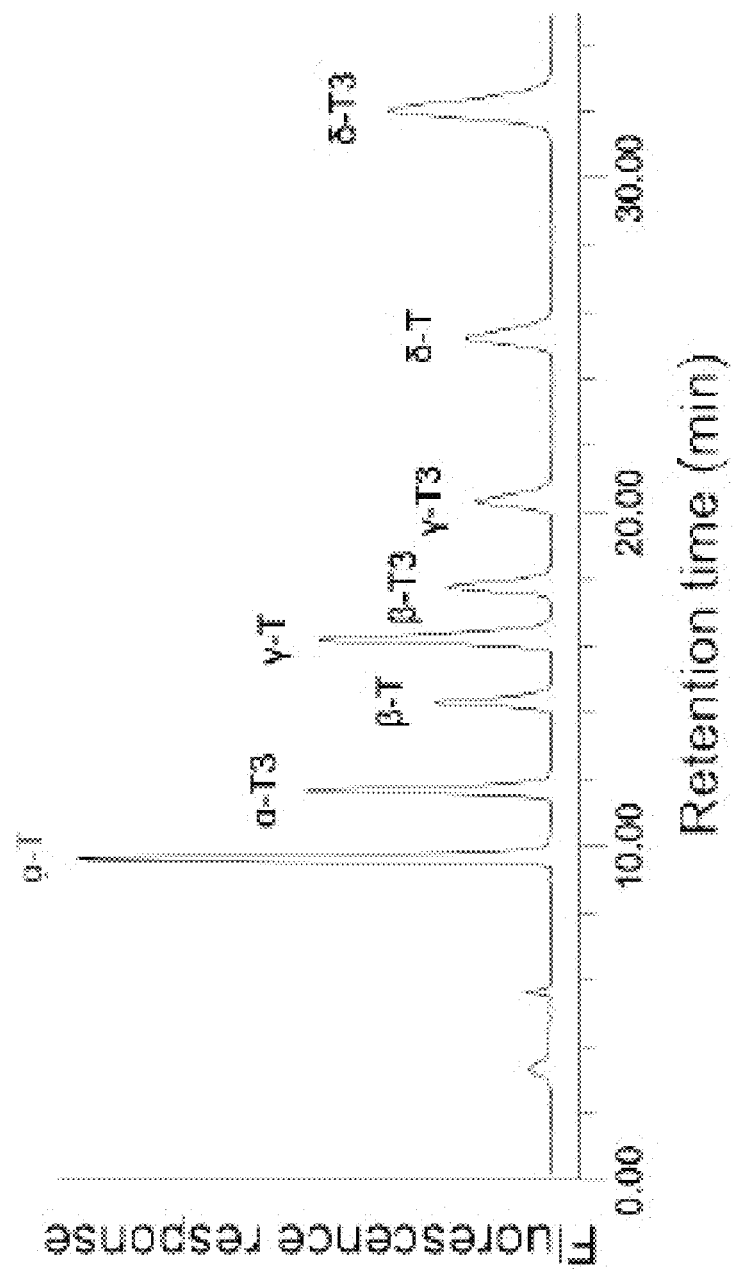
FIG. 1 is a chromatogram obtained using HPLC showing separation of a balanced mixture of tocopherols and tocotrienols on a Phenomenex Luna silica column using hexane-ethyl acetate-acetic acid (97.3:1.8:0.9 v/v/v) at 1.23 ml/min, where the peaks represent: α-T (α-tocopherol), α-T3 (α-tocotrienol), β-T (β-tocopherol), γ-T (γ-tocopherol), β-T3 (β-tocotrienol), γ-T3 (γ-tocotrienol), δ-T (δ-tocopherol) and δ-T3 (δ-tocotrienol)

The compositions and processes discussed herein are merely illustrative of specific manners in which to make and use this invention and are not to be interpreted as limiting in scope.

While the compositions and processes have been described with a certain degree of particularity, it is to be noted that many modifications may be made in the construction and the arrangement of the chemical constituent and function details disclosed herein without departing from the scope of the invention. It is understood that the invention is not limited to the embodiments set forth herein for purposes of exemplification.

Vitamin E tocol compounds have many health benefits with gamma-tocotrienol being the most effective and non-toxic radio-protector identified to date. Rice bran oil deodorizer distillate (RBODD), a by-product of rice bran oil processing, is a rich and abundant source of tocols, including gamma- and delta-tocotrienol. In addition to RBODD, other oils and distillates, such as palm oil, are rich in gamma- and delta-tocotrienols. The process of producing gamma- and/or delta-tocotrienols isolates gamma- and/or delta-tocotrienol from other tocols, especially alpha-tocopherol, which diminishes the radio-protective effect of gamma-tocotrienol. The process disclosed herein uses a fast flash chromatography step to effectively isolate gamma- and/or delta-tocotrienol from the gamma- and/or delta-tocotrienol-rich oil or distillate, and results in a tocol fraction where gamma- and/or delta-tocotrienol comprises 95% of the tocols present, with little to no detectable level of alpha-tocopherol. The process provides a gamma-tocotrienol yield of about 10% and purity in excess of 95% and a delta-tocotrienol yield of about 3% and purity also in excess of 95%. Further, the process may be used to produce purified gamma-tocotrienol, delta-tocotrienol or a mixture of both from tocol-rich concentrates (20-50% total tocols) that are commercially available.

The process of producing purified gamma- and/or delta-tocotrienols from tocol-rich oils or distillates uses a low pressure chromatography method for isolating γ-T3 and/or δ-T3 with little presence of other tocol isomers in the tocotrienol extract. Automated column chromatography systems that operate at pressures of about <75 psi are considered low pressure chromatography, including but not limited to flash chromatography or low pressure liquid chromatography. A binary linear gradient system of 0.8% ethyl acetate-acetic acid (99.1:0.9 v/v) to hexane-acetic acid (99.1:0.9 v/v) (50 min) and 100% ethyl acetate-acetic acid (99.1:0.9 v/v) (5 min) provides a fraction (F) with about 96.5% γ-T3, contained about 69.3 mg/g extract γ-T3, which is about 2-fold lower than the most pure γ-T3 fraction obtained using hexane/ethyl acetate/acetic acid (97.3/1.8/0.9) as an isocratic mobile phase. γ-T3, however, accounted for 96.5% of total tocols with addition of 0.8% EA/AA (with yield of 6% and purity of 90%), while γ-T3 accounted for 47% of total tocols with the isocratic mobile phase.

Due to its excellent health-promoting activities of gamma- and delta-tocotrienol, the d-γ-tocotrienol-rich and/or d-δ-tocotrienol-rich fraction or extract can be incorporated as an active ingredient into pharmaceutical, nutraceutical and food compositions for its antioxidant activity to protect against oxidative stress, which has been linked to many diseases, such as cancer, cardiovascular disease, diabetes, neurodegenerative diseases (e.g., Alzheimer's, Parkinson's), in addition to its hypocholesterolemic and radio-protective abilities. These compositions incorporating the d-γ-tocotrienol-rich and/or d-δ-tocotrienol-rich fraction or extract may further contain protective hydrocolloids, such as gums, proteins, modified starches, binders, film forming agents, encapsulating agents/materials, wall/shell materials, matrix compounds, coatings, emulsifiers, foaming agents, surface active agents, solubilizing agents, e.g., oils, fats, waxes, lecithins etc., adsorbents, carriers, fillers, co-compounds, dispersing agents, wetting agents, processing aids (solvents), flowing agents, flavoring agents, sweetening agents, coloring agents, weighting agents, jellyfying agents, gel forming agents, anti-oxidants, anti-microbial and other preservative agents.

Moreover, a multi-vitamin and mineral supplement may be added to the compositions incorporating the d-γ-tocotrienol-rich and/or d-δ-tocotrienol-rich fraction or extract to obtain an adequate amount of an essential nutrient. The multi-vitamin and mineral supplement may also be useful for disease prevention and protection against nutritional losses and deficiencies due to lifestyle patterns. In addition, the compositions having the d-γ-tocotrienol-rich and/or d-δ-tocotrienol-rich fraction or extract may be incorporated into beverages, e.g., non-alcoholic and alcoholic drinks, soft drinks, sport drinks, energy drinks, fruit juices, lemonades, teas and milk-based drinks, along with other dairy products and/or fortified food and bakery goods.

Further, the pharmaceutical, nutraceutical and food compositions containing the d-γ-tocotrienol-rich and/or d-δ-tocotrienol-rich fraction or extract may be in any galenic formulation that is suitable for administrating to the human body, especially in any form that is conventional for oral administration, e.g., in solid form such as (additives/supplements for) food or feed, food or feed premix, fortified food or feed, tablets, pills, granules, capsules, and effervescent formulations, such as powders and tablets, or in liquid form, such as solutions, emulsions or suspensions, e.g., beverages, pastes and oily suspensions. The pastes may be filled into hard or soft shell capsules, whereby the capsules feature, e.g., a matrix of (fish, swine, poultry, cow) gelatin, plant proteins or ligninsulfonate. Examples for other acceptable forms of administration are transdermal, parenteral and injectable. The pharmaceutical, nutraceutical and food compositions may be in the form of controlled immediate or sustained release formulations.

EXAMPLES

The process of producing purified gamma- and/or delta-tocotrienols from tocol-rich oils or distillates disclosed herein is further illustrated by the following examples, which are provided for the purpose of demonstration rather than limitation. Although RBODD was used in the following examples, any tocol-rich oil or distillate can be used.

Example 1

The objective of Example 1 was to optimize parameters for isolating tocols from RBODD. NP-HPLC analysis of tocol standards was optimized by testing ten (10) mobile phases on a silica column. Extraction of tocols was optimized by testing three concentration solvents (acetonitrile, methanol, ethanol) using various solvent:RBODD ratios (5:1, 10:1, 15:1, 20:1) at two temperatures (4° C. and −20° C.). Hexane/ethyl acetate/acetic acid (97.3:1.8:0.9) provided baseline resolution of all eight tocols. All interactions including solvent*ratio*temperature had a significant effect on tocol levels in the extracts (p<0.0001). Acetonitrile (10:1 ratio, 4° C.) was the most efficient solvent with extracts containing 57.4 mg total tocopherols/g concentrate and 61.4 mg total tocotrienols/g concentrate. These conditions provided extracts with 1.55- and 1.34-fold higher total tocopherols and 2.23- and 1.82-fold higher total tocotrienols than extracts obtained with ethanol and methanol, respectively. Tocol contents in acetonitrile and ethanol extracts were highest when concentrated at 4° C., while tocol content in methanol extracts were highest at −20° C. Under optimal conditions, tocopherol composition was determined to be 34.0% α-T, 3.4% β-T, 44.9% γ-T and 17.4% δ-T and tocotrienol composition was 25.5% α-T3, 72.8% γ-T3 and 1.7% δ-T3.

Apparatus.

Chromatographic measurements were made on an HPLC system consisting of a Waters Alliance 2690 separations module, a Waters 474 fluorescence detector, and Empower Pro 2 Software (Waters Corp., Milford, Mass.). Peaks were detected at an excitation wavelength of 294 nm and an emission wavelength of 326 nm.

Materials.

Rice bran oil deodorizer distillate (RBODD) samples were provided by Riceland Foods (Jonesboro, Ark.). The samples were combined and thoroughly mixed to ensure consistent tocol distribution, and divided into screw-top 50-ml bottles, with 50-60 g per bottle. Samples were stored at 80° C., and individual bottles were thawed when needed for extraction by incubating bottles at room temperature for 4-5 hours, or until product was free of ice crystals. After thawing, each bottle of RBODD was mixed thoroughly before removing subsamples. Standards of α-, β-, γ- and δ-tocotrienols and α-, β-, γ- and δ-tocopherols (94-95% purity) were purchased from Yasoo Health, Inc. (Johnson City, Tenn.).

Mobile Phase Optimization. Mixture of tocol standards (α-, β-, γ- and δ-tocotrienols and tocopherols) in hexane were used for testing. HPLC separations were carried out on a Luna Silica column (250×4.6 mm i.d., 5 μm particle size) (Phenomenex, Torrance, Calif.). The ten mobile phases tested for performance are listed below in Table 1. Run time was 35 min.

TABLE 1

The different mobile phases used for normal-phase HPLC

| No. | Components | Ratio of components | Flow rate |
|---|---|---|---|
| 1 | Hexane-ethyl acetate-acetic acid | 97.3:1.8:0.9 | 1.23 ml/min |
| 2 | Hexane-ethyl acetate-acetic acid | 98.4:0.8:0.8 | 1.23 ml/min |
| 3 | Hexane-1,4-dioxane | 96:4 | 1.23 ml/min |
| 4 | Hexane-tert-butyl methyl ether | 90:10 | 1.23 ml/min |
| 5 | Hexane-tert-butyl methyl ether | 96:4 | 1.23 ml/min |
| 6 | Hexane-isopropanol | 98.8:1.2 | 1.00 ml/min |
| 7 | Hexane-isopropanol | 99:1 | 1.00 ml/min |
| 8 | Hexane-isopropanol | 99.3:0.7 | 1.00 ml/min |
| 9 | Hexane-isopropanol | 99.8:0.2 | 1.00 ml/min |
| 10 | Isooctane-ethyl acetate | 97.6:2.4 | 1.23 ml/min |

Calculation of Peak Resolution.

Peak resolution ($R_S$) was calculated as a measure of the separation between two peaks and the efficiency of the column. This value was expressed as the ratio of the distance between the two peak maxima to the mean value of the peak width at base. A value of $R_S$>1.0 indicates acceptable resolution between peaks, while $R_S$>1.5 indicates complete baseline separation. The peak resolution was calculated as follows, where RT=retention time, W=peak width measured at baseline, a=peak with shorter retention time, b=peak with longer retention time:

$$RS = \frac{2(RTa - RTb)}{Wa + Wb}$$

Concentration of Tocols from RBODD.

Extraction variables tested include solvent, solvent-to-RBODD ratio and concentration temperature (Table 2). Stock samples of 5 g RBODD were mixed with a solvent in the ratios described below in a 250-ml flat-bottom flask (24/40 joint size).

TABLE 2

Concentration variables tested

| Solvent | Solvent: RBODD ratio | Temperature (° C.) |
|---|---|---|
| Acetonitrile | 5:1 | 4 |
| Methanol | 10:1 | −20 |
| Ethanol | 15:1 | |
| | 20:1 | |

The flask was fitted with a reflux condenser and the mixture was brought to boiling then refluxed on a hot plate for 30 min to destroy volatiles and aggregative residues. The mixture was cooled to ambient temperature and stored for 24 hours at 4 or −20° C. in order to precipitate the cold insoluble sterols from the soluble tocols. A sintered glass absorption filter was used to separate the liquid fraction from the insoluble residue. The solvent was evaporated from the liquid fraction using a Speed Vac concentrator (ThermoSavant, Holbrook, N.Y.).

Extraction of Tocols from Concentrates.

Triplicate samples of 0.5 g were taken from stock concentrates prepared using each combination of concentration variables. Each 0.5 g sample was mixed with 4 ml of 5% (w/v) pyrogallol in ethanol and 30 ml of ethanol in a 120-ml flat-bottom flask along with a stir bar. The flask was fitted with a reflux condenser and the mixture heated to boiling. Once boiling, the condenser was removed and 1 ml of 50% (w/v) aqueous potassium hydroxide solution was added to the mixture. The tocols were saponified at 70° C. for 30 min with constant stirring. The flask was placed in an ice bath to stop the reaction. The mixture was transferred to a 500-ml reparatory funnel, and 30 ml diethyl ether and 20 ml distilled water were added. The diethyl ether extraction was repeated two times and the ether fractions were pooled. The pooled diethyl ether was washed three times with 20 ml distilled water, and then filtered through anhydrous sodium sulfate for 30 min to remove any excess water. The diethyl ether was evaporated using the Speed Vac concentrator.

Sample Preparation for HPLC Analysis.

Extracts were resolubilized with hexane to a volume to 5 ml and filtered through a 0.45 μm Millipore membrane before injection into the HPLC. The tocols were analyzed in triplicate using the HPLC conditions.

Quantification of Tocols.

The tocol peaks for each sample were identified and the concentration was calculated by comparing peak area against the standard curve equation.

$$\text{tocol concentration } (ppm) = \frac{\text{peak area} - \text{intercept}}{\text{slope}} \quad \text{Equation 1}$$

This value was converted to display mg tocol isomer/g RBODD extract.

$$\frac{\text{mg } tocol}{\text{g extract}} = \frac{tocol \text{ concentration} \times \text{final volume} \times \text{dilution factor}}{\text{initial sample weight}} \quad \text{Equation 2}$$

Statistical Analysis.

Reported values represent the mean of duplicate samples prepared using each gradient system. Isomer concentrations and relative percentages for each fraction were analyzed by means comparison with student's t-test ($p<0.05$) (JMP software v. 10.0, Cary, N.C.).

Analysis by Normal Phase-HPLC.

With NP-HPLC, tocol separation occurs by adsorption based on polarity, which is determined by the degree of methylation on their chromanol rings. The unsaturation on the C16 tail makes tocotrienols slightly more polar than their corresponding tocopherols. Beta and gamma isomers have the same number of methyl groups, making complete separation challenging. Gamma isomers have 7,8-dimethyls, which increases their asymmetry and polarity compared to beta isomers with 5,8-dimethyls. The observed elution order in this example corresponded with structural characteristics of the tocols and was as follows: α-T (9.6 min), α-T3 (11.6 min), β-T (14.3 min), γ-T (16.2 min), β-T3 (17.7 min), γ-T3 (20.3 min), δ-T (25.2 min), δ-T3 (32.0 min).

Peak resolution was best using an isocratic mobile phase consisting of hexane (HX)/ethyl acetate (EA)/acetic acid (AA) (97.3:1.8:0.9, v/v) (FIG. 1). Resolution ranged from 1.4 to 4.1, indicating that the eight vitamin E isomers were baseline separated. The lowest resolution ($R_s=1.4$) was seen between γ-T and β-T3, due to their structural similarities.

Figure 2:
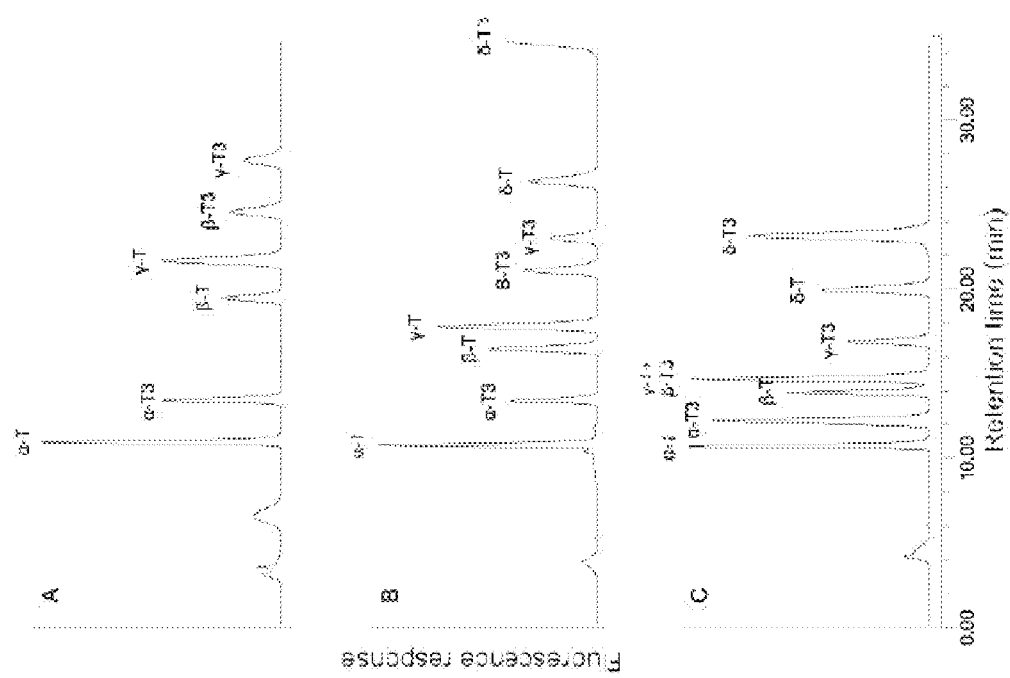
FIG. 2 is a chromatogram obtained using HPLC showing separation of a balanced mixture of tocopherols and tocotrienols on a Phenomenex Luna silica column using various mobile phases: (A) hexane-ethyl acetate-acetic acid (98.4:0.8:0.8 v/v/v) at 1.23 ml/min; (B) hexane-1,4-dioxane (96:4 v/v) at 1.23 ml/min; and (C) hexane-methyl-tert-butyl ether (90:10 v/v) at 1.23 ml/min.
Figure 3:
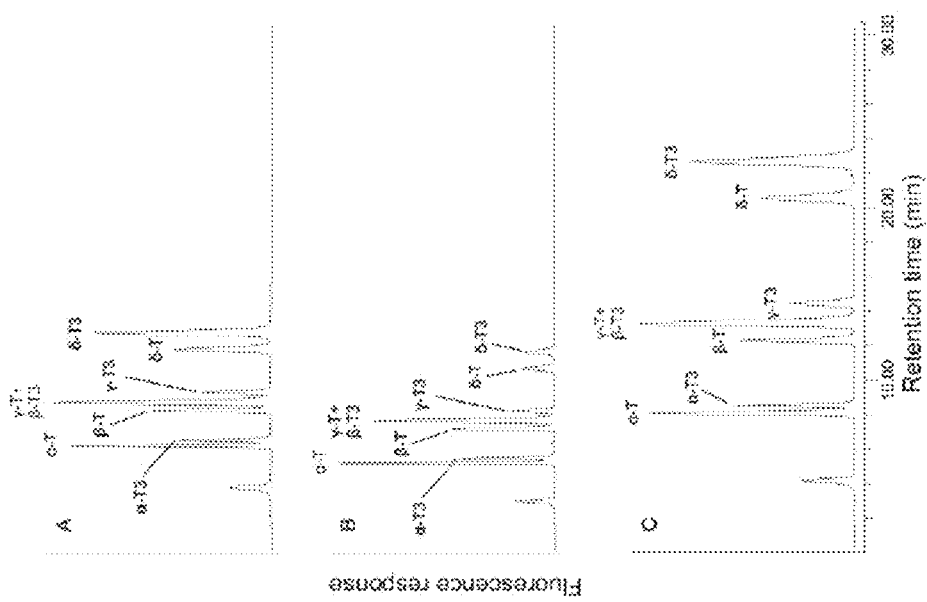
FIG. 3 is a chromatogram obtained using HPLC showing separation of a balanced mixture of tocopherols and tocotrienols on a Phenomenex Luna silica column using mixtures of isopropanol in hexane as mobile phases: (A) hexane-isopropanol (98.8:1.2 v/v) at 1.00 ml/min; (B) hexane-isopropanol (99:1 v/v) at 1.00 ml/min; and (C) hexane-isopropanol (99.3:0.7 v/v) at 1.00 ml/min.
Figure 4:
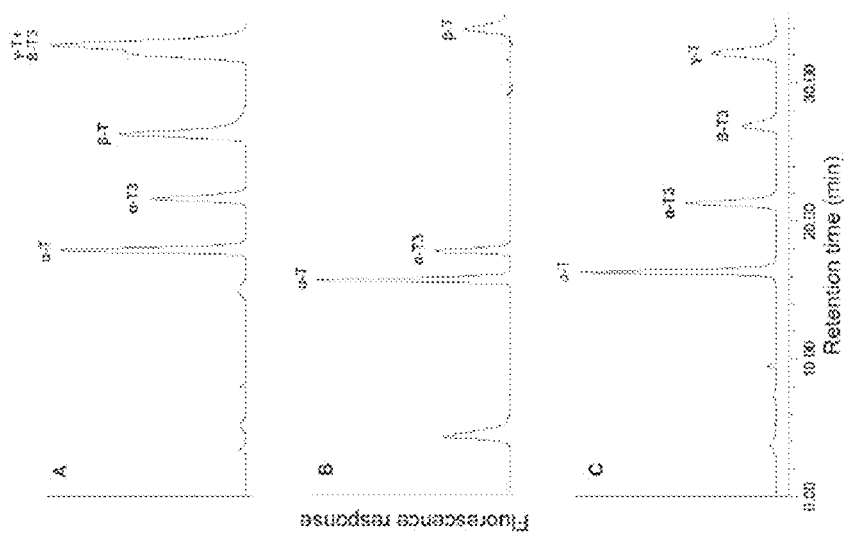
FIG. 4 is a chromatogram obtained using HPLC showing separation of a balanced mixture of tocopherols and tocotrienols on a Phenomenex Luna silica column using various mobile phases: (A) hexane-methyl-tert-butyl ether (96:4 v/v) at 1.23 ml/min; (B) hexane-isopropanol (99.8:0.2 v/v) at 1.00 ml/min; and (C) isooctane-ethyl acetate (97.6:2.4 v/v) at 1.23 ml/min.

There was a lack of separation of beta and gamma isomers with use of HX/MTBE and HX/IPA mobile phases (FIGS. 2 and 3). Co-elution of these isomers resulted in $R_s=0$ for those mobile phases, indicating incomplete separation of the vitamers. Use of 1,4-dioxane (4%) in hexane provided satisfactory separation of all eight E-vitamers, though resolution of beta and gamma isomers was not as strong as when HX-EA-AA (97.3:1.8:0.9 v/v/v) was used. The chromatograms obtained using HX-EA-AA (98.4:0.8:0.8 v/v/v), HX-MTBE (96:4 v/v) HX-IPA (99.8:0.2 v/v), and isooctane-EA (97.6:2.4 v/v) failed to resolve the peaks within the 35-minute run time, making these mobile phases less than ideal for tocol analysis in this example (FIGS. 2A, 2B, 3A and 4C).

Retention Time Drift with New Column.

Figure 5:
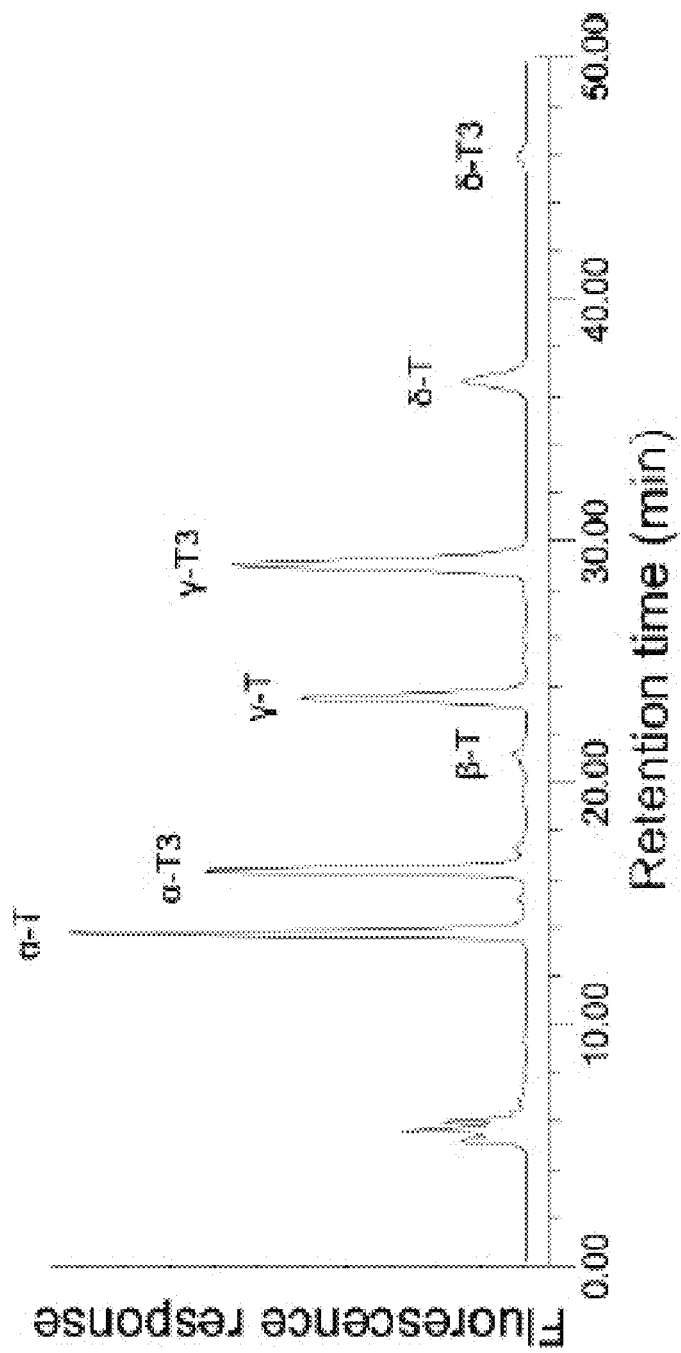
FIG. 5 is a chromatogram of tocols in rice bran oil deodorizer distillate.

A new Luna Silica column (250×4.6 mm i.d., 5 μm particle size) (Phenomenex, Torrance, Calif.) was purchased for analyzing tocols in RBODD samples. This coincided with a retention time drift for all tocol isomers, resulting in a new run time of 50 min. A chromatogram of tocols in an RBODD sample is seen in FIG. 5. In all samples, only seven tocol isomers were detected: α-T, β-T, γ-T, δ-T, α-T3, γ-T3 and δ-T3. The elution order remained the same, though the new retention times were as follows: α-T (13.8 min), α-T3 (16.4 min), β-T (21.2 min), γ-T (23.5), γ-T3 (29.0 min), δ-T (36.6 min), δ-T3 (45.9 min).

Concentration of Tocols from RBODD.

Total tocol concentration was significantly affected by solvent*ratio*temperature ($p<0.0001$).

Solvent Effects.

Three solvents, including acetonitrile, methanol and ethanol were tested for their effects on tocol concentration from RBODD. The level of total tocols was highest when acetonitrile was used, followed by methanol and ethanol. Tocol content ranged from 118.8 mg/g using acetonitrile (10:1 at 4° C.) to 76.5 mg/g using methanol (10:1 at −20° C.) to 64.5 mg/g using ethanol (10:1 at 4° C.). Acetonitrile in 10:1 ratio at 4° C. proved to be the most efficient combination of variables for all isomers, especially γ-T3 (44.6 mg/g). This concentration is significantly higher than those obtained using methanol (10:1 at −20° C.) and ethanol (10:1 at 4° C.) at their best ratio/temperature combinations (25.5 mg/g and 20.0 mg/g, respectively) (Table 3). Ethanol fractionation is commonly used in industrial purification of tocopherols from soybean oil deodorizer distillate because sterols are insoluble in cold ethanol while tocopherols are soluble, though some tocopherols co-precipitate with sterols. This example, however, found acetonitrile to be the ideal solvent for tocol concentration from RBODD.

TABLE 3

Tocol concentrations in RBODD obtained using optimal ratio for each solvent at 4 and −20° C.[†]

| Temp (° C.) | Solvent | Ratio | Tocopherols | | | | Tocotrienols | | | Total Tocols[§] |
|---|---|---|---|---|---|---|---|---|---|---|
| | | | α-T | β-T | γ-T | δ-T | α-T3 | γ-T3 | δ-T3 | |
| 4 | Acetonitrile | 10:1 | 19.5[a] (16.4)[b] | 1.9[a] (1.6)[b] | 25.8[a] (21.7)[b] | 10.2[a] (8.6)[b] | 15.6[a] (13.2)[a] | 44.6[a] (37.6)[a] | 1.1[a] (0.9)[b] | 118.8[a] |
| 4 | Methanol | 15:1 | 14.3[b] (19.4)[a] | 1.3b[c] (1.8)[b] | 18.6[b] (25.3)[a] | 6.8b[c] (9.2)[b] | 7.8[b] (10.6)[b] | 23.9b[c] (32.6)[c] | 0.8a[b] (1.0)[b] | 73.3[b] |
| 4 | Ethanol | 10:1 | 12.8[bc] (19.8)[a] | 1.1[c] (1.7)[b] | 16.8[bc] (26.1)[a] | 6.3[c] (9.8)[b] | 6.9[b] (10.7)[b] | 20.0[cd] (30.9)[cd] | 0.6[b] (0.9)[b] | 64.5[bc] |
| −20 | Acetonitrile | 5:1 | 6.4[d] (12.2)[c] | 1.7[ab] (3.2)[a] | 8.2[d] (15.5)[c] | 9.4[a] (17.7)[a] | 6.8[b] (12.9)[a] | 19.2[cd] (36.4)[ab] | 1.1[a] (2.1)[a] | 52.8[c] |
| −20 | Methanol | 10:1 | 12.0[bc] (15.7)[b] | 1.7[ab] (2.3)[b] | 19.9[b] (26.0)[a] | 9.2[ab] (12.1)[b] | 7.0[b] (9.2)[c] | 25.8[b] (33.7)[bc] | 0.9[ab] (1.1)[b] | 76.5[b] |
| −20 | Ethanol | 15:1 | 11.1[c] (20.3)[a] | 1.2[c] (2.2)[b] | 14.1[c] (25.8)[a] | 5.8[c] (10.6)[b] | 5.7[b] (10.5)[b] | 16.0[d] (29.4)[d] | 0.7[b] (1.3)[b] | 54.5[c] |

[†]Means of three replicates (mg/g concentrate). Values in parenthesis refer to the percent distribution of each tocol.
Means within columns followed by the same letter are not significantly different (p < 0.05).
[§]Tocols: tocopherols + tocotrienols.
T, tocopherol; T3, tocotrienol.

Solvent-to-RBODD Ratio Effects.

Figure 6:
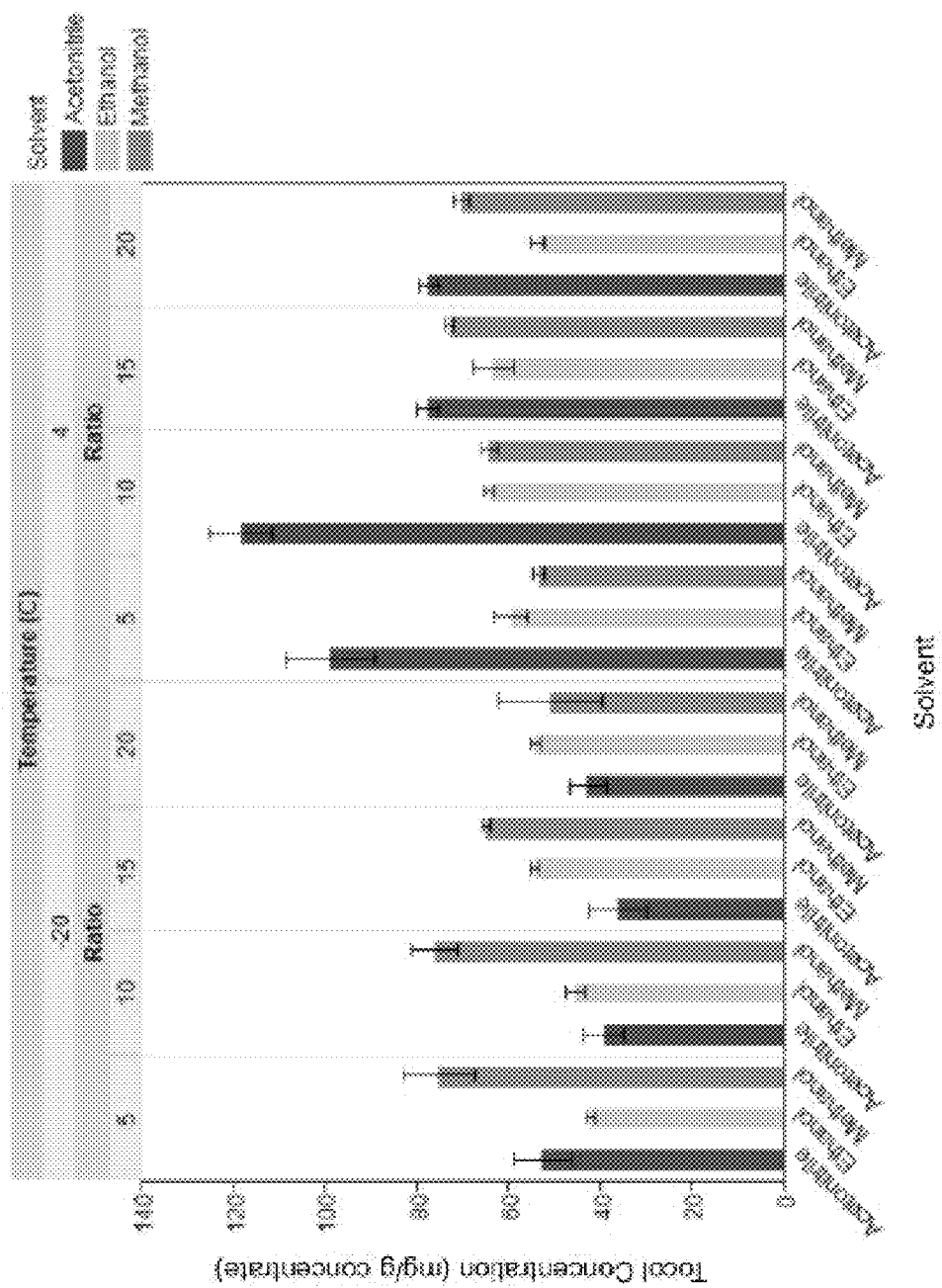
FIG. 6 graphically illustrates total tocol concentration in RBODD using all combinations of concentration variables, where the bars represent ±SEM (n=3)

The optimal solvent-to-RBODD ratio was 10:1 across all solvents (FIG. 6). For the best solvents at each temperature (acetonitrile at 4° C. and methanol at −20° C.) the higher ratios (15:1, 20:1) were less efficient in tocol concentration. This may be due to excess solvent facilitating tocol crystallization, specifically at −20° C.

Tocol Distribution in RBODD.

The tocol composition of RBODD obtained using acetonitrile (10:1 at 4° C.) is shown in Table 4 below:

TABLE 4

Tocol Composition of RBODD Deodorizer

| | Tocol (percent) | |
|---|---|---|
| | Tocopherol | Tocotrienol |
| Alpha | 34 | 25 |
| Beta | 3 | — |
| Gamma | 45 | 73 |
| Delta | 18 | 2 |

Figure 7:
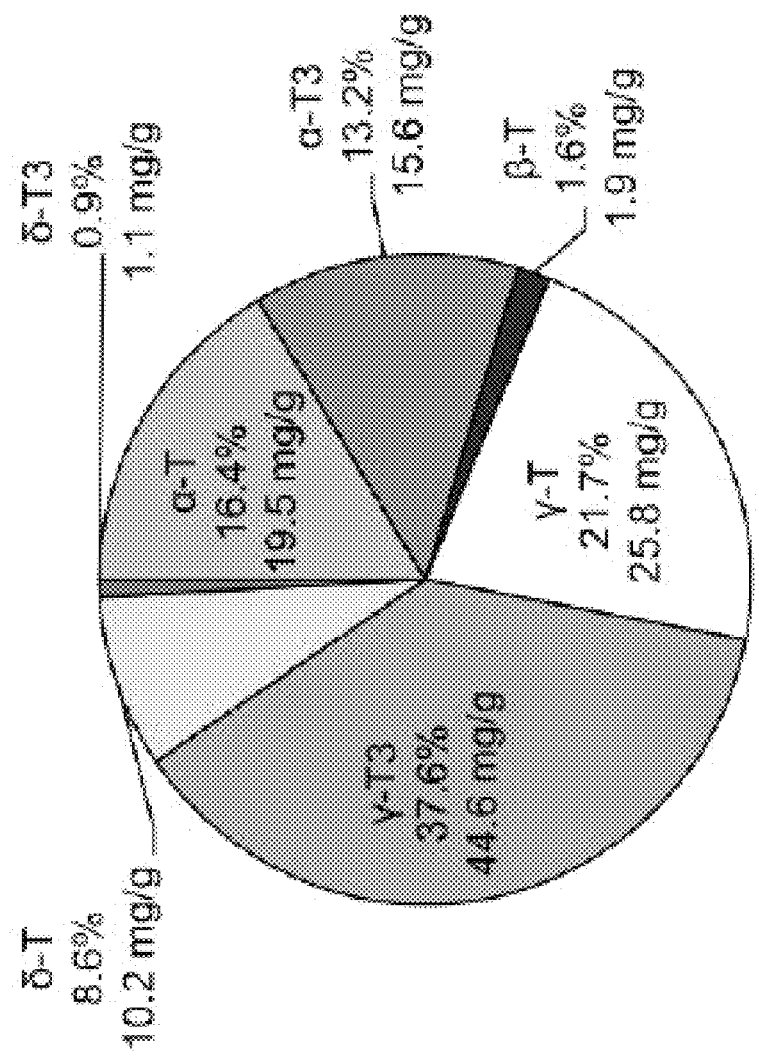
FIG. 7 graphically illustrates the distribution of tocols in RBODD.

The distribution of the tocol isomers in RBODD is shown in FIG. 7. γ-T and γ-T3 were the predominant tocols, followed by the alpha isomers. α-T has shown an antagonistic effect on health benefits of γ-T3 and δ-T3. In order to produce a tocol-rich fraction from RBODD that is high in γ-T3, purification measures were developed in Example 2 to minimize the proportion of alpha isomers present in the fraction.

Example 2

The objective of Example 2 was to test various flash chromatography conditions for the purification of a fraction with a high proportion of γ-T3 and a minimal amount of alpha isomers from tocol extract obtained from rice bran oil deodorizer distillate. Load size (0.125 g, 0.250 g, 0.500 g, 1.000 g), sample cartridge type (prepacked silica cartridge, empty cartridge+Celite 545) and mobile phase gradient (varying proportions of hexane-acetic acid (99.1:0.9 v/v) and ethyl acetate-acetic acid (99.1:0.9 v/v)) were evaluated. Among the loading sizes tested, the smallest sample size (~0.125 g) provided the best peak resolution. Loading the sample onto a silica cartridge allowed for enhanced peak separation, due to a double pass of sample through silica gel. A linear addition of 0.8% ethyl acetate/acetic acid (99.1:0.9 v/v) to hexane/acetic acid (99.1:0.9 v/v) provided a fraction with 69.3 mg/g extract γ-T3, which was 2-fold lower than the most pure γ-T3 fraction obtained using hexane/ethyl acetate/acetic acid (97.3/1.8/0.9) as an isocratic mobile phase. However, γ-T3 purity was 96.5% (with no alpha isomers present) with addition of 0.8% EA/AA compared to 47.0% with the isocratic mobile phase. Therefore, the ideal flash chromatography method should be determined based on end usage of γ-T3.

Apparatus.

Separations were made using a CombiFlash Rf system with a 340CF evaporative light scattering detector (ELSD) (Teledyne Isco, Inc., Lincoln, Nebr.). Fractions were analyzed by normal phase HPLC consisting of a Waters Alliance 2690 separations module, a Waters 474 fluorescence detector, and Empower 2 Pro Software (Waters Corp., Milford, Mass.). Peaks were detected at an excitation wavelength of 294 nm and an emission wavelength of 326 nm. HPLC separations were carried out on a Luna Silica column (250×4.6 mm i.d., 5 μm particle size) (Phenomenex, Torrance, Calif.). Mobile phase was hexane-ethyl acetate-acetic acid (97.3/1.8/0.9 v/v/v, 1.23 ml/min).

Materials.

RBODD samples were obtained from Riceland Foods (Jonesboro, Ark.). The samples were combined and thoroughly mixed to ensure consistent tocol distribution, and divided into screw-top 50-ml bottles, with 50-60 g per bottle. Samples were stored at −80° C., and individual bottles were thawed when needed for extraction by incubating at room temperature for 4-5 hours, or until product was free of ice crystals. Each bottle of RBODD was mixed thoroughly before removing individual sample. Standards of α-, β-, γ- and δ-tocotrienols and α-, β-, γ- and δ-tocopherols (94-95% purity) were purchased from Yasoo Health, Inc. (Johnson City, Tenn.).

Sample Preparation. Tocol extracts were prepared as prepared in Example 1 above. In short, 5 g RBODD were mixed with 50 ml acetonitrile in a 250-ml flat-bottom flask (24/40 joint size). The flask was fitted with a reflux condenser and the mixture was brought to boiling then refluxed on a hot plate for 30 min to destroy volatiles and aggregative residues. The mixture was cooled to ambient temperature and stored for 24 hr at 4° C. in order to precipitate the cold insoluble sterols from the soluble tocols. A sintered glass absorption filter was used to separate the liquid fraction from the insoluble residue. The solvent was evaporated from the liquid fraction using a Speed Vac concentrator (ThermoSavant, Holbrook, N.Y.) to produce tocol concentrate. The resulting tocol concentrate (~1.75 g) was mixed with 14 ml of 5% (w/v) pyrogallol in ethanol and 105 ml ethanol in a 250-ml flat-bottom flask along with a stir bar. The flask was fitted with a reflux condenser and the mixture was heated to boiling. Once boiling, the condenser was removed and 3.5 ml of 50% (w/v) aqueous potassium hydroxide solution was added to the mixture. The tocols were saponified at 70° C. for 30 min with constant stirring. The flask was placed in an ice bath to stop the reaction. The mixture was transferred to a 500-ml reparatory funnel, and 105 ml diethyl ether and 70 ml distilled water were added. The diethyl ether extraction was repeated two times and the ether fractions were pooled. The pooled diethyl ether was washed three times with 70 ml distilled water and then filtered through anhydrous sodium sulfate for 30 min to remove any excess water. The diethyl ether was evaporated using the Speed Vac concentrator to produce tocol extract.

Load Capacity.

The loading study was conducted using prepared tocol extract and 12 g RediSep Rf Gold normal phase silica columns (20-40 μm particle size) (Teledyne Isco, Inc., Lincoln, Nebr.). This column size has a sample load capacity 0.1-1.0%. The following load sizes were tested for peak resolution: 0.125 g, 0.250 g, 0.500 g and 1.000 g. Samples were dissolved in hexane, mixed with 5 g Celite 545 (Sigma-Aldrich, St. Louis, Mo.), dried using a rotary evaporator and packed into 5-g sample load cartridges. Single samples were used in order to preserve extract stock extract. In this Example 2, the mobile phase consisted of hexane/ethyl acetate/acetic acid (97.3:1.8:0.9 v/v) for 17 min, followed by neat ethyl acetate for 3 min.

Sample Cartridge Type.

The optimal sample load size was tested on two types of RediSep Rf solid load cartridges (Teledyne Isco, Inc., Lincoln, Nebr.): 5-g empty disposable cartridge and 5-g prepacked disposable silica cartridge. The empty cartridge was prepared by filling the cartridge with a slurry mixture of the dissolved sample and Celite 545 (supporting media). For the prepacked silica cartridge preparation, sample was pipetted onto the top of the cartridge. The ideal cartridge was chosen based on peak resolution. In this Example 2, the mobile phase consisted of hexane-ethyl acetate-acetic acid (97.3:1.8:0.9 v/v/v) for 17 min, followed by neat ethyl acetate for 3 min.

Gradient Optimization.

The flash chromatography system allows for easy control of mobile phase gradient. The mobile phase consisted of a binary gradient of hexane-acetic acid (99.1:0.9 v/v) (A) and ethyl acetate-acetic acid (99.1:0.9 v/v) (B). The flow rate was 30 ml/min with various linear gradients as follows:

TABLE 5

Binary gradients tested on flash chromatography

| Time | Gradient System ID Number | | | |
|---|---|---|---|---|
| | 1 | 2 | 3 | 4 |
| 0-50 min | 0-0.8% B | 0-1.3% B | 0-1.8% B | 0-2.3% B |
| 50-55 min | 100% B | 100% B | 100% B | 100% B |

The four (4) binary gradient systems in Table 5 were compared against an optimal mobile phase for tocol HPLC analysis, which was an isocratic system ("System 5") consisting of hexane-ethyl acetate-acetic acid (97.3:1.8:0.9 v/v/v). The isocratic mobile phase was run for 50 min, followed by neat ethyl acetate at 50-55 min to ensure removal of all compounds from System 5.

Comparison of Two Flash Chromatography Gradient Systems for Isolation of Gamma-Tocotrienol.

The binary gradient system in Table 5 that provided fractions with the highest levels of γ-T3 with minimal presence of other isomers was chosen for tocol quantification. Duplicate samples of 0.125 g extract were pipetted onto pre-packed silica cartridges and fractionated by flash chromatography using Systems 1 and 5. Fractions were collected, dried down using the Speed Vac concentrator and brought to 5 ml with hexane. Samples were filtered through a 0.45 μm Millipore membrane before injection into the HPLC. The tocols were analyzed in duplicate using the HPLC conditions described above in Example 1.

Quantification of Tocols.

Similar to Example 1, the tocol peaks for each sample were identified and the concentration was calculated by comparing peak area against the standard curve equation (Equation 1 above) and then converted to display mg tocol isomer/g RBODD extract (Equation 2 above).

Statistical Analysis.

Similar to Example 1, reported values represent the mean of duplicate samples prepared using each gradient system. Isomer concentrations and relative percentages for each fraction were analyzed by means comparison with student's t-test ($p<0.05$) (JMP software v. 10.0, Cary, N.C.).

Load Capacity.

Figure 9:
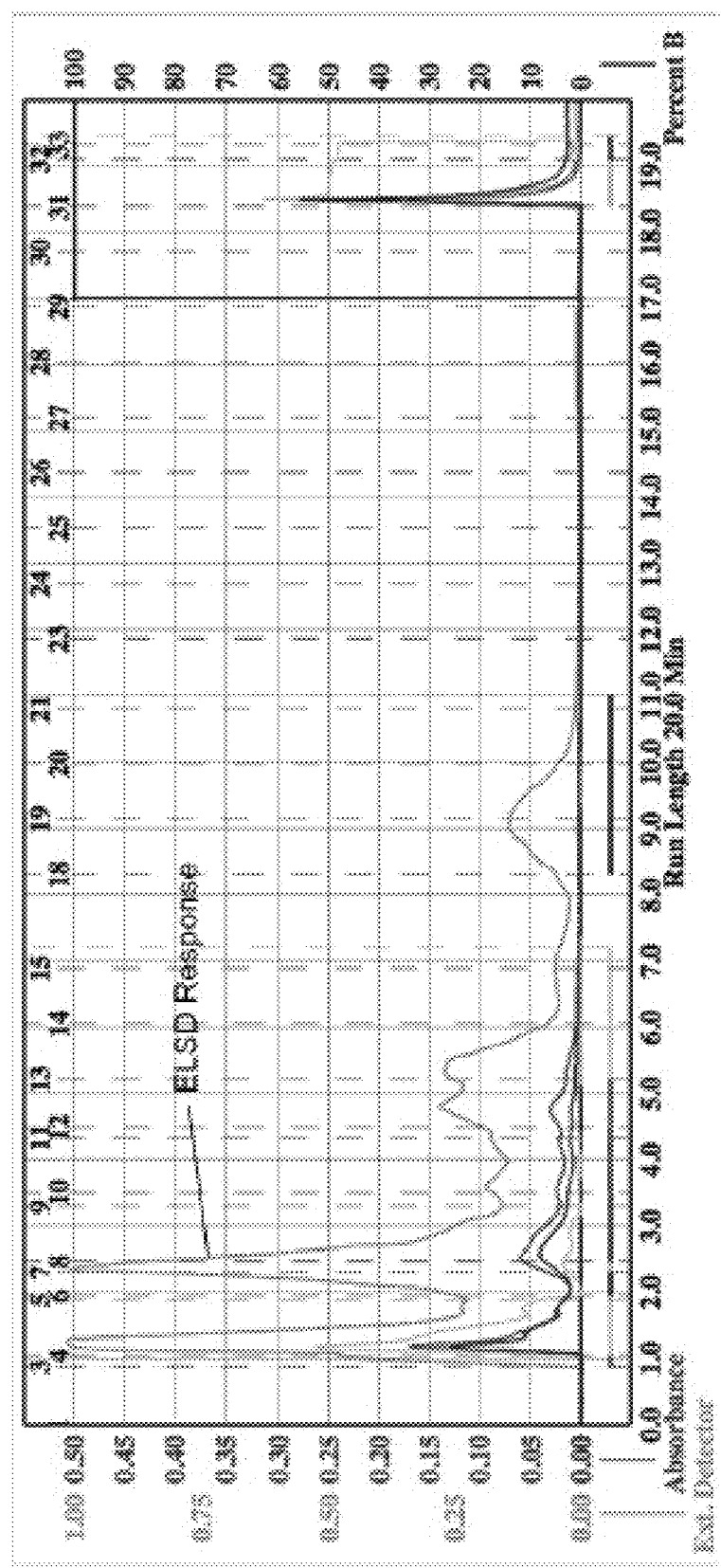
FIG. 9 is a chromatogram obtained using flash chromatography with 0.260 g extract mixed with Celite 545 and packed into an empty 5-g cartridge, where the gradient mobile phase was 100% hexane-ethyl acetate-acetic acid (97.3:1.8:0.9 v/v/v) (17 min) and 100% ethyl acetate (3 min)
Figure 10:
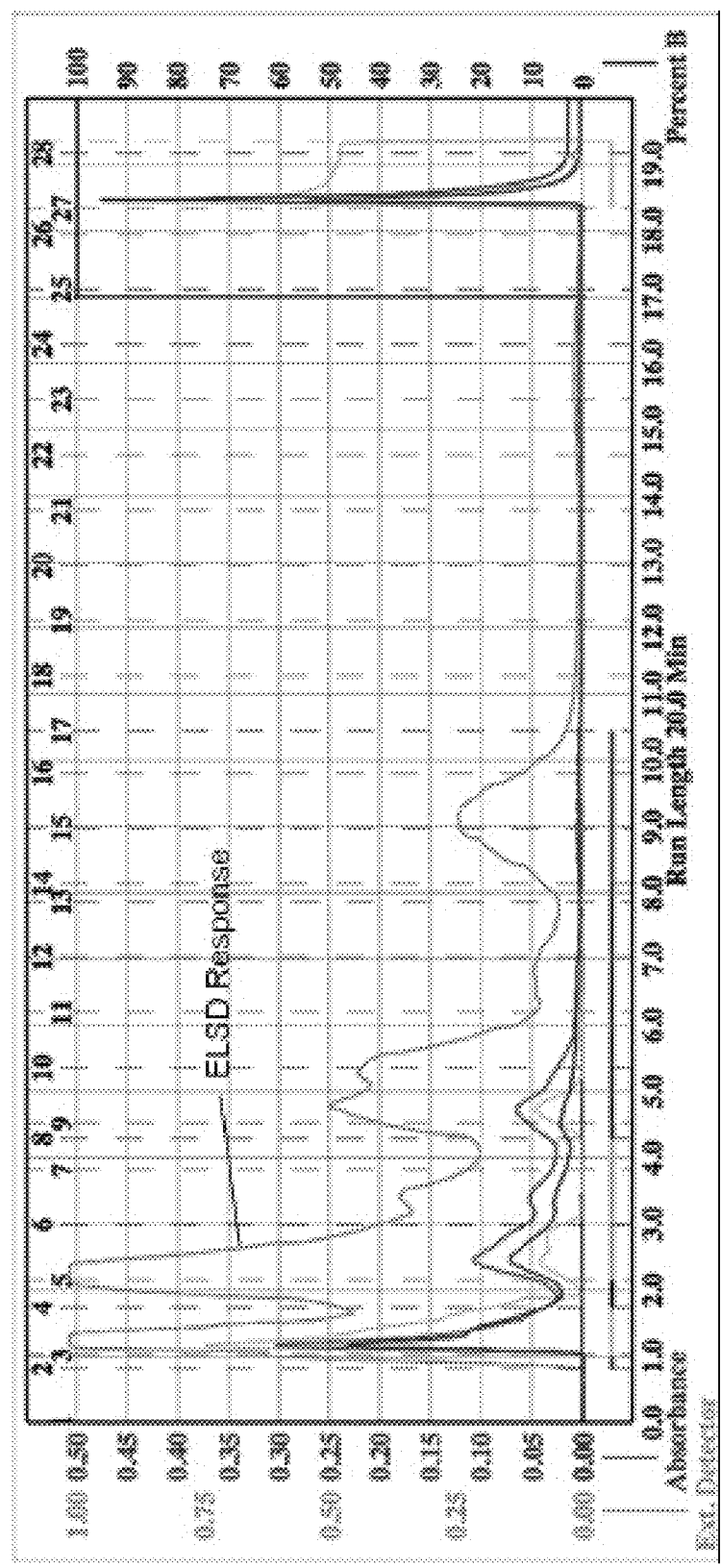
FIG. 10 is a chromatogram obtained using flash chromatography with 0.502 g extract mixed with Celite 545 and packed into an empty 5-g cartridge, where the gradient mobile phase was 100% hexane-ethyl acetate-acetic acid (97.3:1.8:0.9 v/v/v) (17 min) and 100% ethyl acetate (3 min)
Figure 11:
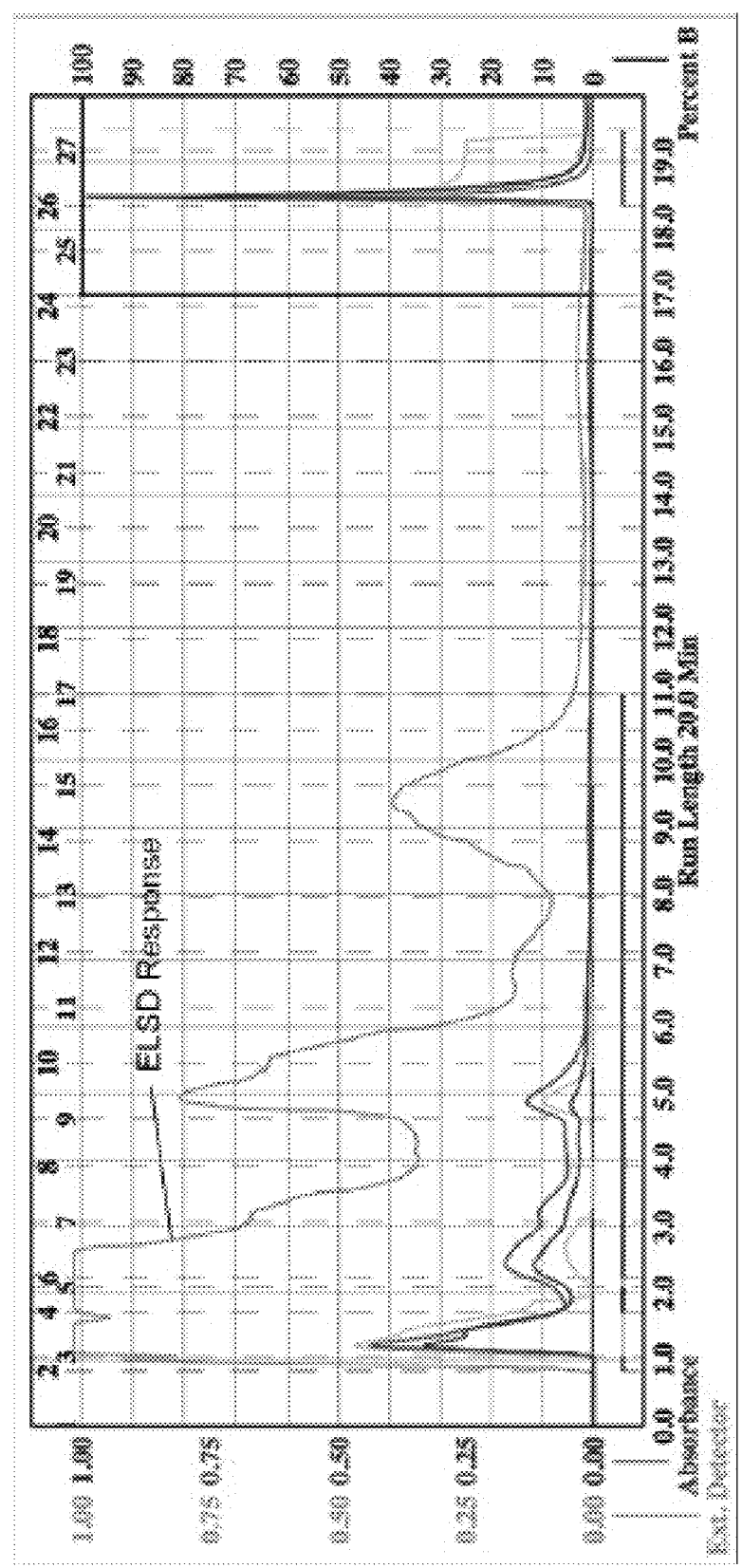
FIG. 11 is a chromatogram obtained using flash chromatography with 1.007 g extract mixed with Celite 545 and packed into an empty 5-g cartridge, where the gradient mobile phase was 100% hexane-ethyl acetate-acetic acid (97.3:1.8:0.9 v/v/v) (17 min) and 100% ethyl acetate (3 min)

Extract samples were loaded onto Celite and packed into empty sample cartridges. Exact load sizes tested for peak resolution were: 0.125 g (FIG. 8), 0.260 g (FIG. 9), 0.502 g (FIG. 10) and 1.007 g (FIG. 11). For all samples, ELSD detected 6-7 peaks. At the higher load sizes, peak separation was poor and peaks were very broad with some exceeding the threshold of the detector. As load size decreased, resolution improved with the smallest load size providing best peak resolution. This was expected, as separation efficiency generally decreases as loading amount increases due to the larger sample size exceeding the column capacity. Although all load sizes tested fall within the capacity of the column (60 mg to 1.2 g), some overload occurred in the larger sample sizes (0.502 g and 1.007 g). This was evident by an overlap of neighboring peaks and a decrease in peak resolution.

Sample Cartridge Type.

Figure 8:
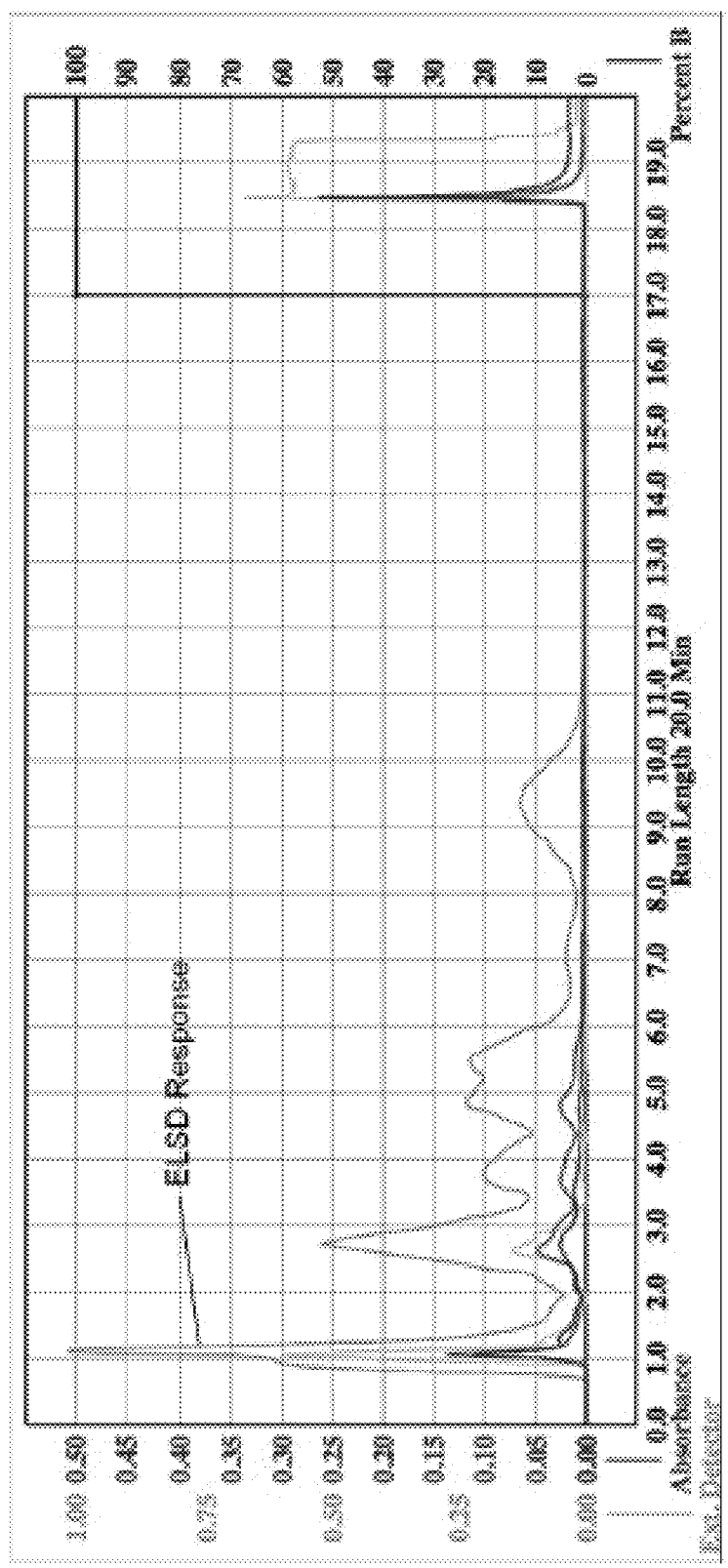
FIG. 8 is a chromatogram obtained using flash chromatography with 0.125 g extract mixed with Celite 545 and packed into an empty 5-g cartridge, where the gradient mobile phase was 100% hexane-ethyl acetate-acetic acid (97.3:1.8:0.9 v/v/v) (17 min) and 100% ethyl acetate (3 min)
Figure 12:
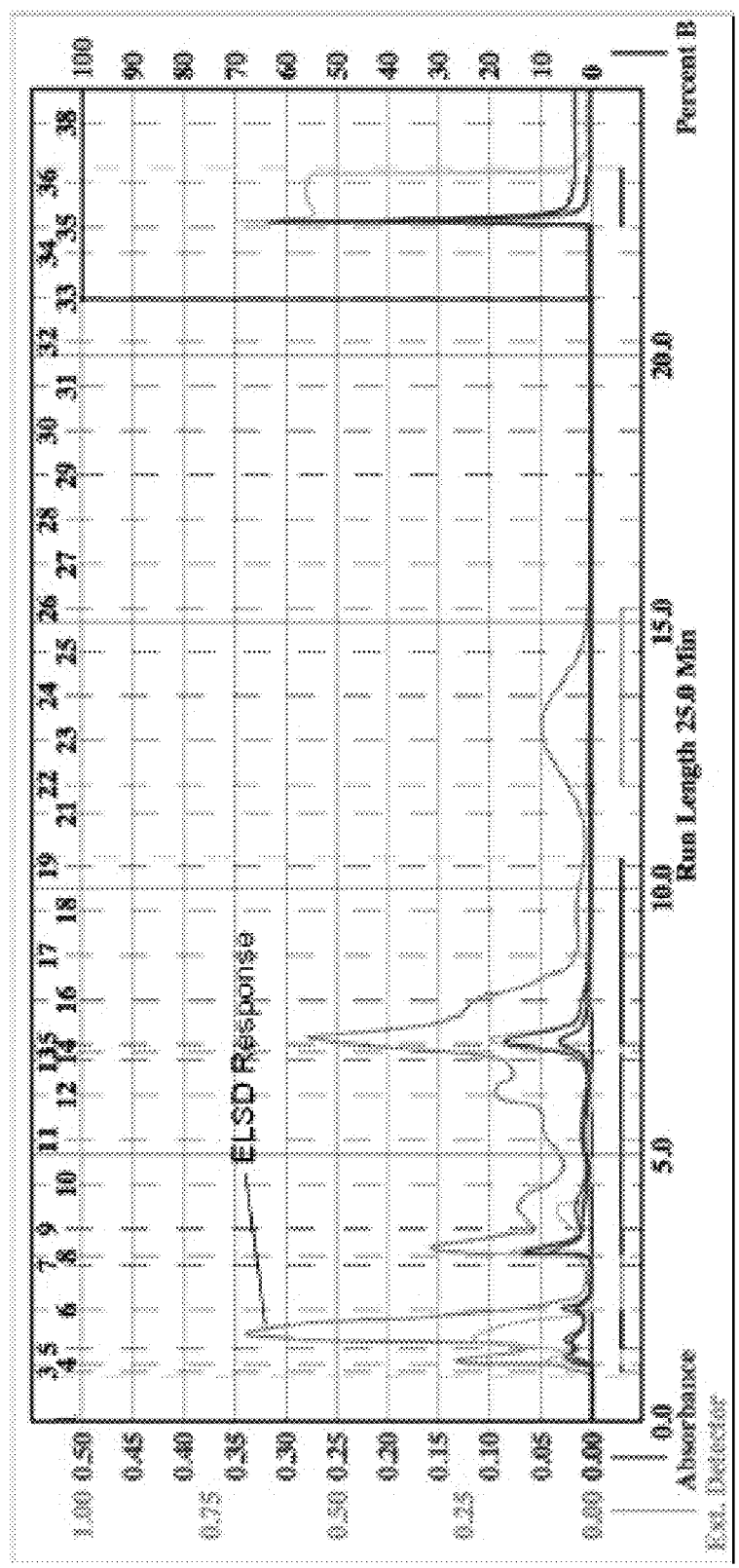
FIG. 12 is a chromatogram obtained using flash chromatography with 0.129 g extract loaded into a pre-packed 5-g silica cartridge, where the gradient mobile phase was 100% hexane-ethyl acetate-acetic acid (97.3:1.8:0.9 v/v/v) (17 min) and 100% ethyl acetate (3 min)

The sample size that provided best resolution in the loading capacity study (~0.125 g) was used to determine which cartridge type gave best peak separation. When sample was mixed with Celite 545 and packed into an empty cartridge, 6 peaks were resolved (FIG. 8). These peaks had slight shoulders, indicating tocol isomers were not fully separated. When sample was placed onto a pre-packed silica cartridge, 9-10 peaks were detected, which were more clearly separated due to the double pass of sample through silica (FIG. 12). Use of the silica pre-cartridge allows more time for interaction between tocols and silica, resulting in greater separation of the compounds.

Gradient Optimization.

Figure 13:
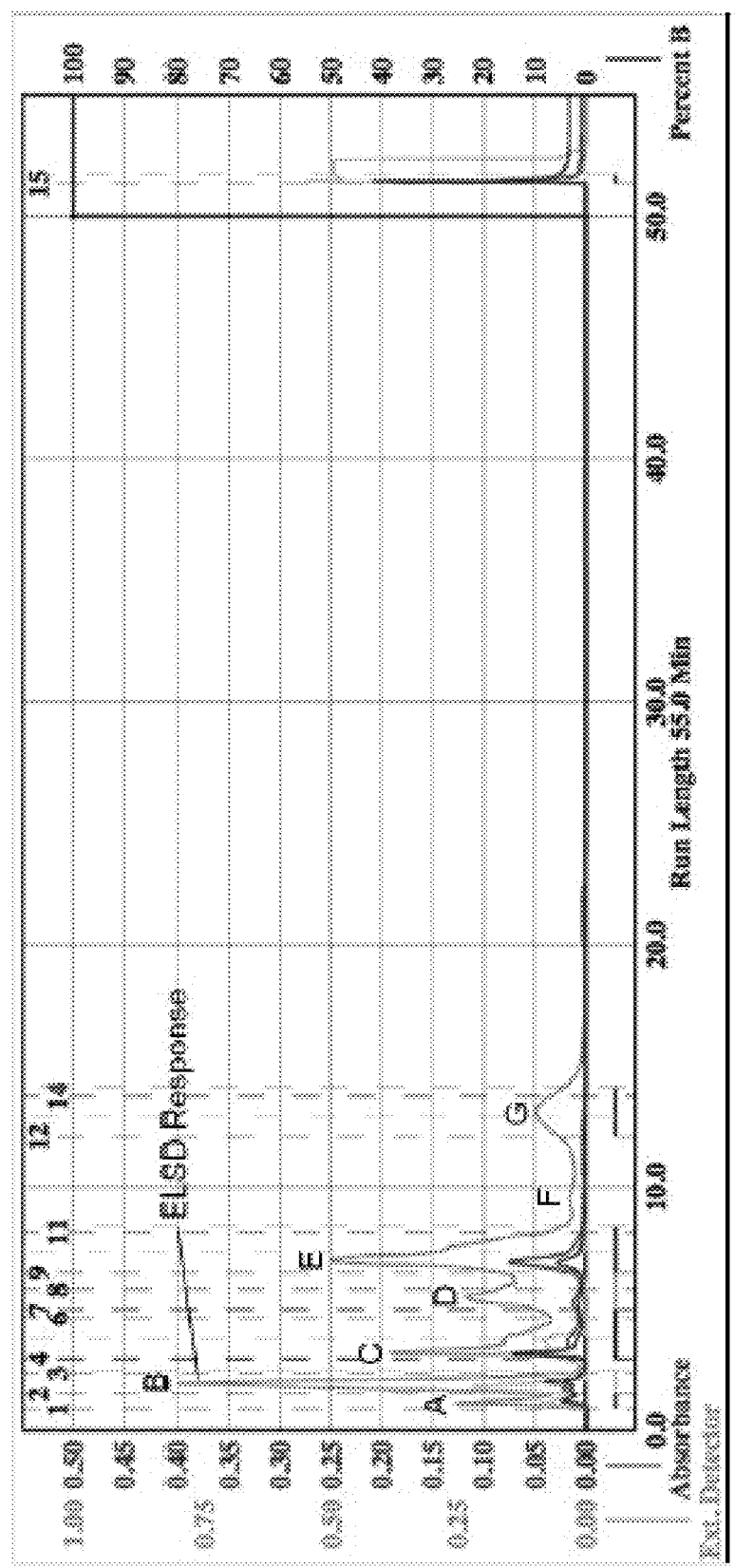
FIG. 13 is a chromatogram obtained using flash chromatography with 0.127 g extract loaded onto a 5-g prepacked silica cartridge, where the gradient mobile phase was 100% hexane-ethyl acetate-acetic acid (97.3:1.8:0.9 v/v/v) (50 min) and 100% ethyl acetate (5 min), and where the letters indicate individual peaks.
Figure 14:
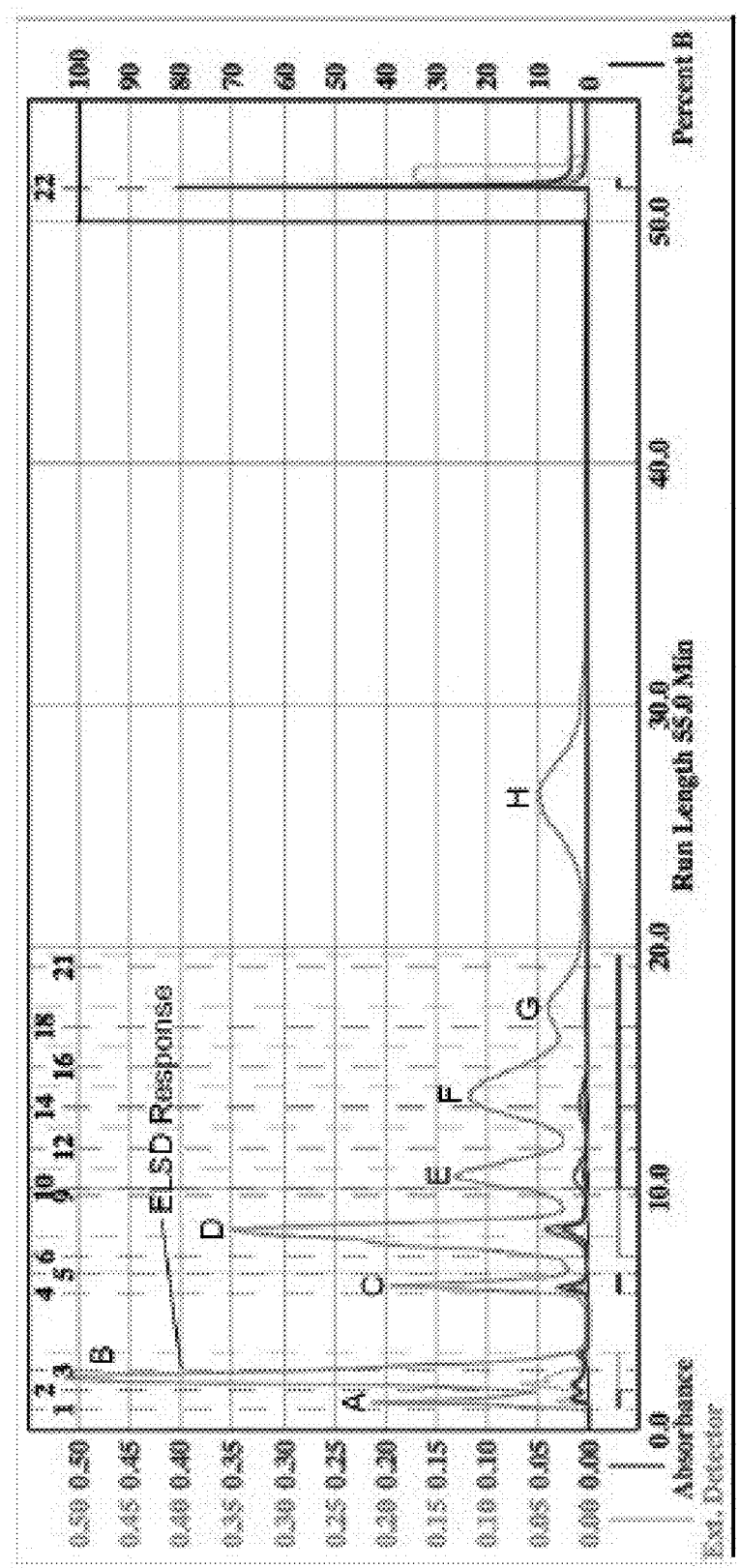
FIG. 14 is a chromatogram obtained using flash chromatography with 0.132 g extract loaded onto a 5-g prepacked silica cartridge, where the gradient mobile phase was slow addition of 0.8% ethyl acetate-acetic acid (99.1:0.9 v/v) to hexane-acetic acid (99.1:0.9 v/v) (50 min) and 100% ethyl acetate-acetic acid (99.1:0.9 v/v) (5 min), and where the letters indicate individual peaks.
Figure 15:
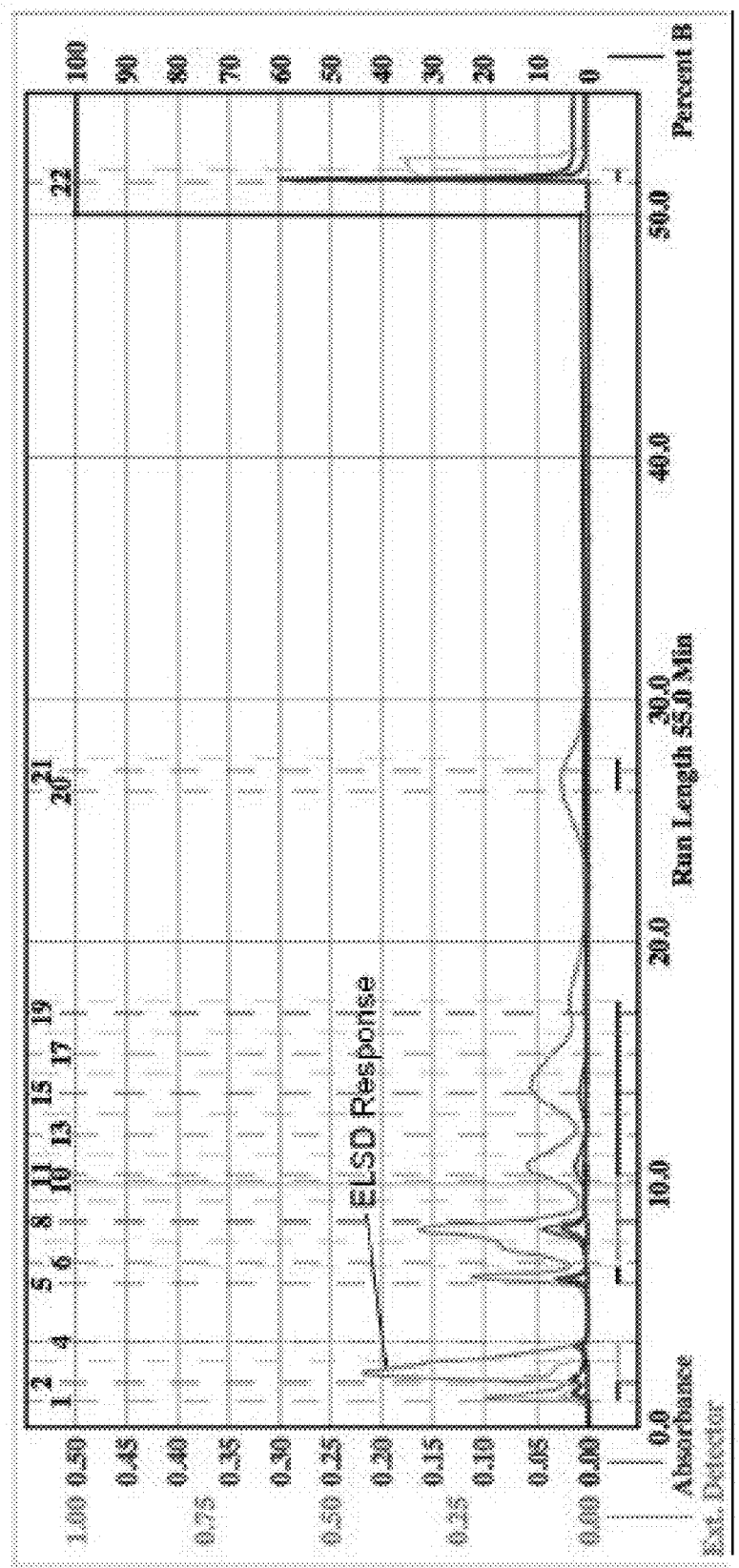
FIG. 15 is a chromatogram obtained using flash chromatography with 0.127 g extract loaded onto a 5-g prepacked silica cartridge, where the gradient mobile phase was slow addition of 1.3% ethyl acetate-acetic acid (99.1:0.9 v/v) to hexane-acetic acid (99.1:0.9 v/v) (50 min) and 100% ethyl acetate-acetic acid (99.1:0.9 v/v) (5 min)
Figure 16:
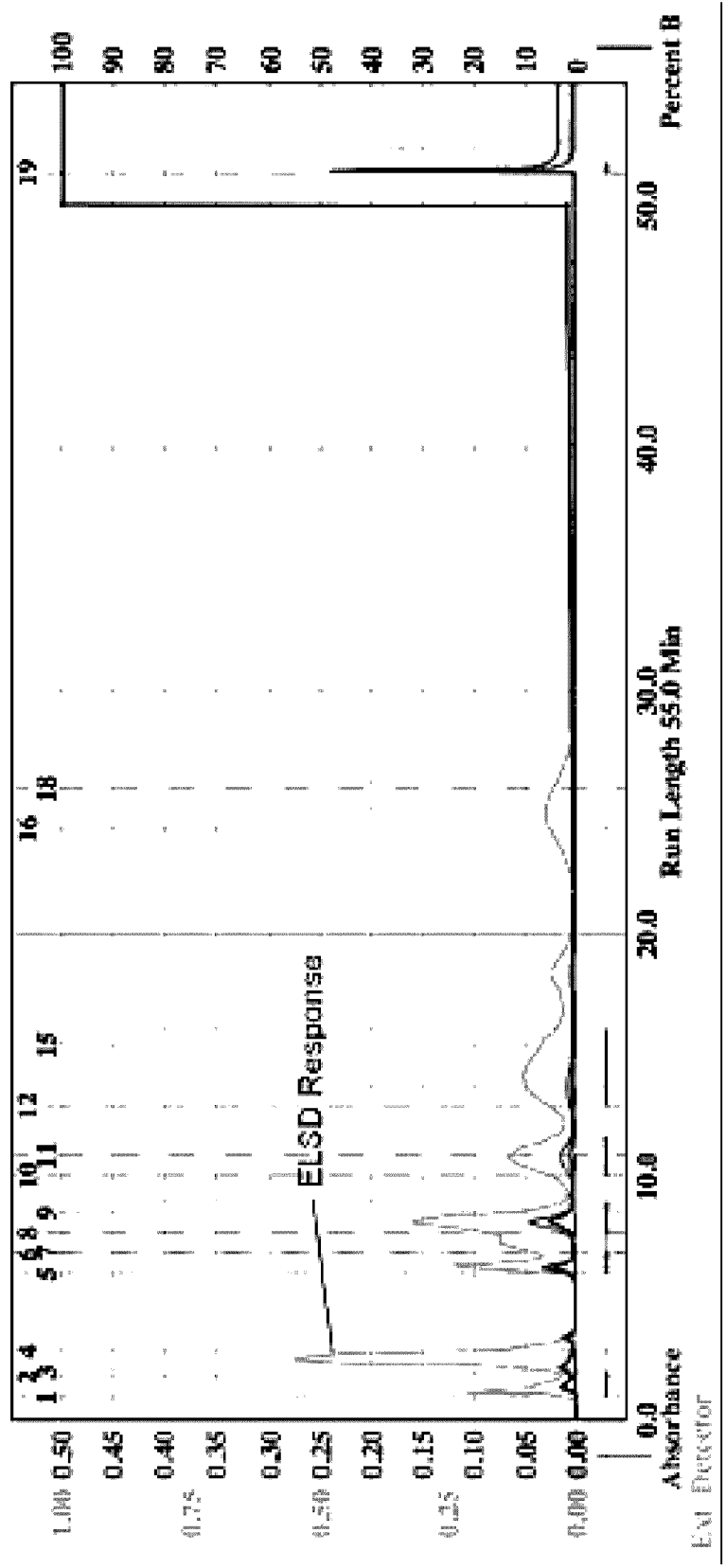
FIG. 16 is a chromatogram obtained using flash chromatography with 0.130 g extract loaded onto a 5-g prepacked silica cartridge, where the gradient mobile phase was slow addition of 1.8% ethyl acetate-acetic acid (99.1:0.9 v/v) to hexane-acetic acid (99.1:0.9 v/v) (50 min) and 100% ethyl acetate-acetic acid (99.1:0.9 v/v) (5 min)
Figure 17:
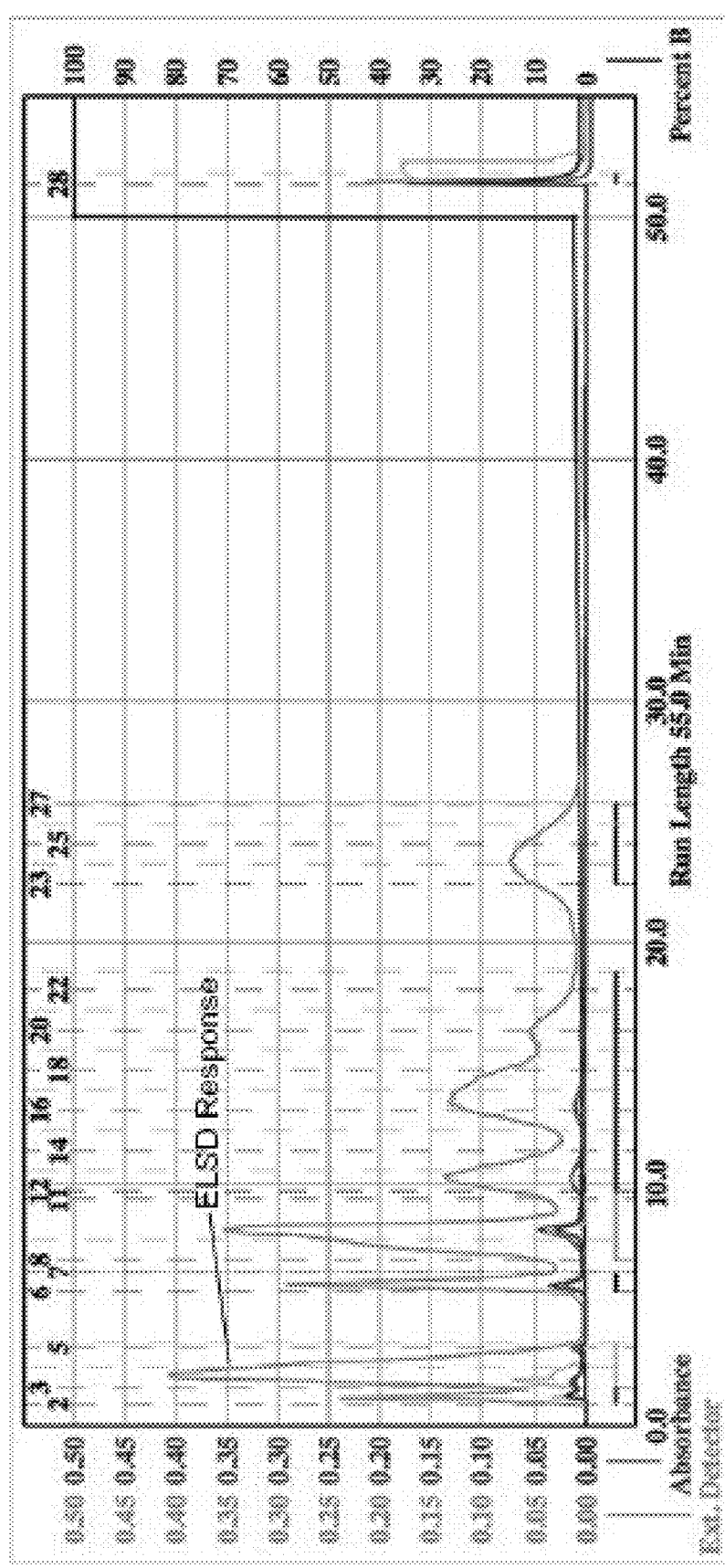
FIG. 17 is a chromatogram obtained using flash chromatography with 0.130 g extract loaded onto a 5-g prepacked silica cartridge, where the gradient mobile phase was slow addition of 2.3% ethyl acetate-acetic acid (99.1:0.9 v/v) to hexane-acetic acid (99.1:0.9 v/v) (50 min) and 100% ethyl acetate-acetic acid (99.1:0.9 v/v) (5 min)
Figure 18:
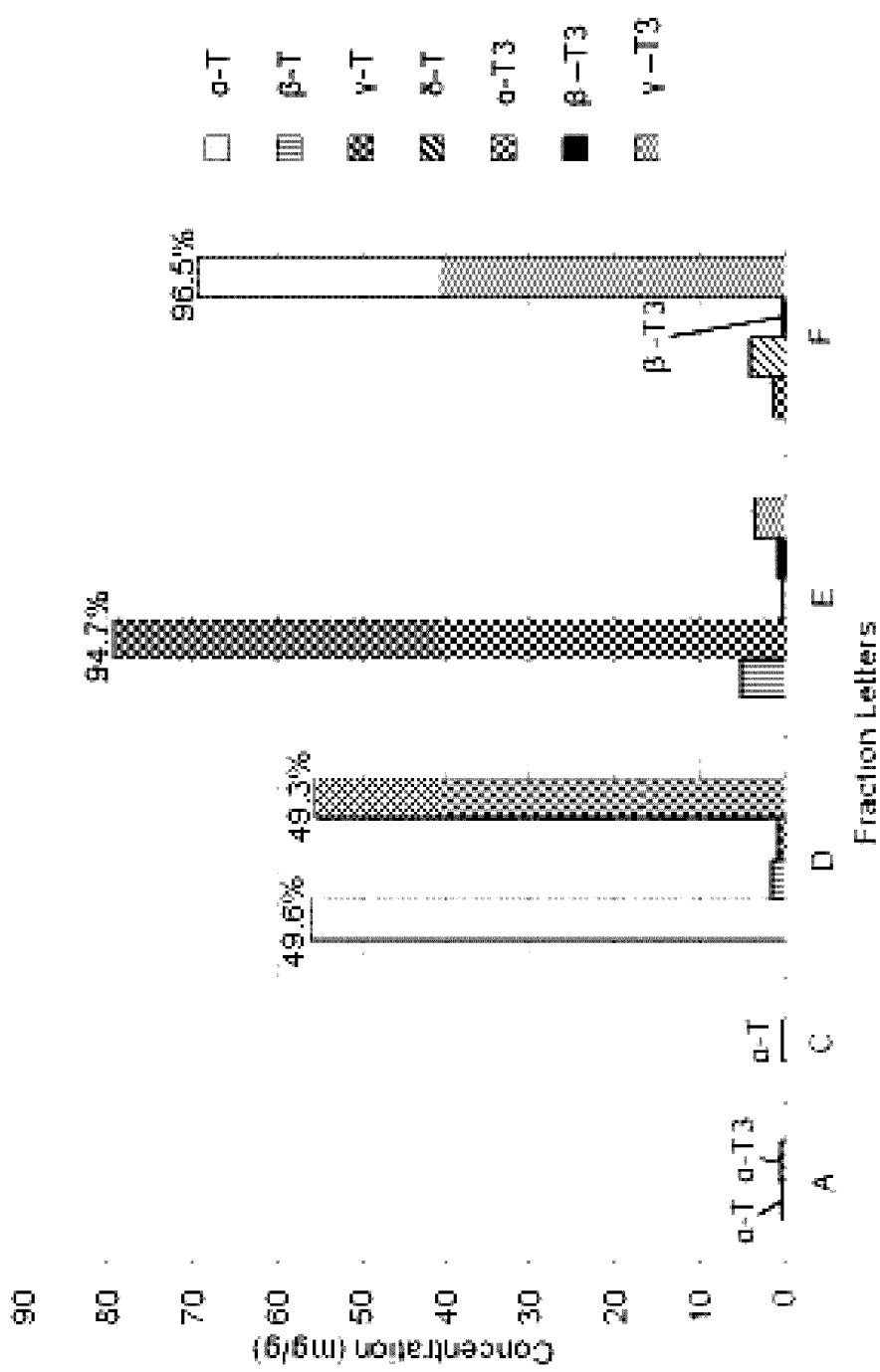
FIG. 18 graphically illustrates the composition of fractions obtained using System 1 gradient mobile phase of 0.8% ethyl acetate-acetic acid (99.1:0.9 v/v) to hexane-acetic acid (99.1:0.9 v/v) (50 min) and 100% ethyl acetate-acetic acid (99.1:0.9 v/v) (5 min), where the fraction letters correspond with letters in FIG. 14, and where the relative percentages of the predominant isomers in each fraction are shown.
Figure 19:
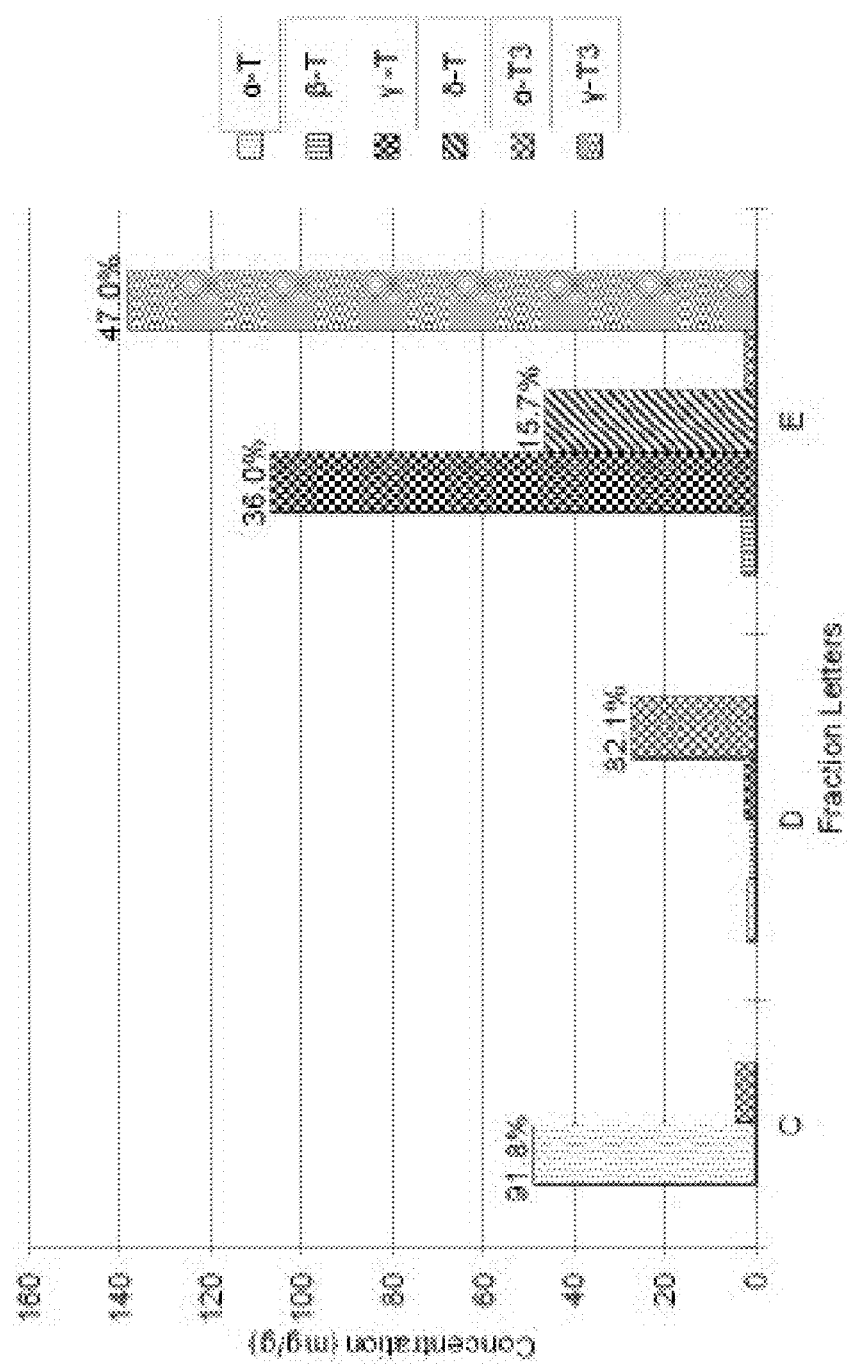
FIG. 19 graphically illustrates the composition of fractions obtained using obtained System 5 gradient mobile phase of 100% hexane-ethyl acetate-acetic acid (97.3:1.8:0.9 v/v/v) (50 min) and 100% ethyl acetate (5 min), where the fraction letters correspond with letters in FIG. 13, and where the relative percentages of the predominant isomers in each fraction are shown.

The flash chromatograms for the isocratic mobile phase and the four binary gradient systems (Table 5) are shown in FIGS. 13-17. Table 6 shows the tocol compositions of the labeled fractions in FIGS. 13 and 14. Compounds eluted very quickly (within 15 min) using 100% HX-EA-AA (97.3/1.8/0.9 v/v/v), resulting in co-elution (FIG. 13). The binary gradient system which involved adding 0.8% EA-AA (99.1:0.9 v/v) to HX-AA (99.1:0.9 v/v) (FIG. 14) provided the best peak resolution of all gradients tested. As the proportion of EA-AA (99.1:0.9 v/v) was increased, peak resolution decreased though co-elution was still evident by slight shoulders (FIGS. 15-16). Peaks were analyzed by HPLC to determine which fractions contained the highest proportion of γ-T3 compared to α-T and α-T3. Addition of 0.8% EA-AA yielded more fractions with high levels of γ-T3 and low presence of other isomers, especially alpha isomers (FIG. 14). Addition of 2.3% of the ethyl acetate mixture was unable to separate the isomers (FIG. 17). This resulted in fractions with both alpha and gamma isomers present in large amounts, and no fractions that contained only γ-T3.

their relative percentages is shown for each fraction obtained using these methods in Table 5 and FIGS. 18 and 19. Elution order followed the expected pattern, with early fractions containing alpha isomers, followed by beta, gamma and delta isomers. δ-T3 was not present in detectable amounts in any of the fractions.

System 1 (0.8% EA-AA gradient) fractions A and B contained very small levels of alpha tocols, while fractions G and H did not contain tocols in any detectable amount. The majority of tocols eluted in fractions D, E and F for system 1. Fraction D was composed mostly of equal amounts of α-T and α-T3, with negligible amounts of β-T and γ-T. Composition shifted from alpha isomers to gamma isomers in fraction E, with 79.2 mg γ-T/g extract and minor amounts of β-T, β-T3 and α-T3. γ-T3 content was low in fraction E (3.7 mg/g), but it comprised 96.5% of the tocols present in fraction F with 69.3 mg/g. In a follow-up study using identical flash chromatography conditions (System 1) described above, the yield and purity of γ-T3 obtained from fraction F were 11% and 54%, respectively. Through further fractionation of fraction F, a γ-T3 yield and purity of 6% and 90%, respectively, was obtained.

System 5 (isocratic conditions) fractions A, B, F and G contained no tocols, with the majority of tocols eluting in fractions C, D and E. As with the equivalent fraction in System 1, System 5 fraction C contained mostly α-T and T3, with concentrations of 48.9 mg/g and 4.5 mg/g, respectively.

TABLE 6

Concentration and relative percentage of tocol isomers for fractions obtained by flash chromatography using different gradient conditions[†]

| Gradient | Fraction | Tocopherols | | | | Tocotrienols | | | | Total Ts | Total T3s | Total Tocols[§] |
|---|---|---|---|---|---|---|---|---|---|---|---|---|
| | | α-T | β-T | γ-T | δ-T | α-T3 | β-T3 | γ-T3 | δ-T3 | | | |
| 0.8% EA/AA[1] | A | 0.3 (33.3) | | | | 0.6 (66.7) | | | | 0.3 (33.3) | 0.6 (66.7) | 0.9 |
| 0.8% EA/AA | C | 0.3 (100) | | | | | | | | 0.3 (100) | | 0.3 |
| 0.8% EA/AA | D | 55.9 (49.6) | 1.6 (1.3) | 0.9 (0.8) | | 55.5 (49.3) | | | | 57.1 (50.7) | 55.5 (49.3) | 112.6 |
| 0.8% EA/AA | E | | 5.3 (5.5) | 79.2 (94.7) | | 0.3 (0.3) | 1.0 (1.0) | 3.7 (3.8) | | 81.9 (97.4) | 5.0 (5.2) | 84.4 |
| 0.8% EA/AA | F | | | 1.5 (1.7) | 4.2 (4.8) | | 0.4 (0.5) | 69.3 (96.5) | | 5.7 (6.5) | 69.5 (96.8) | 72.3 |
| 0.8% EA/AA | G | | | | | | | | | | | |
| 0.8% EA/AA | H | | | | | | | | | | | |
| Isocratic[2] | A | | | | | | | | | | | |
| Isocratic | B | | | | | | | | | | | |
| Isocratic | C | 48.9 (91.8) | | | | 4.5 (8.2) | | | | 48.9 (91.8) | 4.5 (8.2) | 53.4 |
| Isocratic | D | 1.6 (5.1) | 1.5 (4.9) | 2.4 (7.9) | | 27.1 (82.1) | | | | 5.4 (17.9) | 27.1 (82.1) | 32.4 |
| Isocratic | E | | 3.1 (1.0) | 106.7 (36.0) | 46.2 (15.7) | 2.3 (0.7) | | 138.2 (47.0) | | 156.0 (52.7) | 139.4 (47.3) | 295.3 |
| Isocratic | F | | | | | | | | | | | |
| Isocratic | G | | | | | | | | | | | |

[†]Means of two replicates (mg/g extract). Values in parentheses refer to the relative percent distribution of each tocol per total concentration of tocols in each respective fraction.
[1]Indicates the gradient system consisting of 0.8% ethyl acetate-acetic acid (99.1:0.9 v/v) + hexane-acetic acid (99.1:0.9 v/v) (50 min) and 100% ethyl acetate-acetic acid (99.1:0.9 v/v) (5 min) (System 1).
[2]Indicates the gradient system consisting of 100% hexane-ethyl acetate-acetic acid (97.3:1.8:0.9 v/v/v) (50 min) and 100% ethyl acetate (5 min) (System 5).
[§]Tocols: tocopherols + tocotrienols.
T, tocopherol; T3, tocotrienol.

Comparison of Two Flash Chromatography Gradient Systems for Isolation of Gamma-Tocotrienol.

Tocols were quantified for both the fractions obtained by the 0.8% EA-AA gradient (FIG. 14) as well as the isocratic mobile phase (FIG. 13). The concentration of tocols and their Fraction D contained mostly α-T3 (27.1 mg/g) with minor amounts of α-T, β-T and γ-T. Fraction E consisted of 47% γ-T3 with 138.2 mg/g. However, this fraction still contained a large amount of γ-T (106.7 mg/g) as well as low levels of β-T, δ-T and α-T3.

Both of the methods in Example 2 were able to isolate fractions that contain a high proportion of γ-T3 with minimal presence of alpha isomers, with much higher γ-T3 purity. This example used hexane-ether elution by flash chromatography to prepare a tocol-rich fraction from rice bran extracts, which contained only 33.5% γ-T3, in addition to 6% α-T, 12.5% α-T3, 10% δ-T and T3, 9.6% d-$P_{21}$-T3, 10.4% d-$P_{25}$-T3 and 8% unidentified tocol isomers.

Relative percentages of the predominant isomer in each fraction are shown in FIGS. 18 and 19. Although System 5 provided a single fraction with a higher concentration of γ-T3, System 1 provided a significantly more pure fraction of γ-T3 (96.5% of total tocols in fraction F compared to 47% of total tocols in fraction E with System 5) (p=0.0055). Therefore, end usage of γ-T3 may determine which binary gradient system is preferred. Clinical trials with γ-T3 may prefer System 1 due to the purity of the γ-T3 fraction. The opposite trend was seen for α-T, with a significantly more pure (91.8% of total tocols) fraction with System 5 (fraction C) compared to 49.6% of total tocols α-T fraction with System 1 (fraction D) (p=0.0002). δ-T purity was also significantly higher with System 5 (fraction E) compared to System 1 (fraction F) (p=0.0243), though γ-T purity was better with System 1 (fraction E) compared to System 5 (fraction E) (p=0.0083).

The results of this example provide a fast flash chromatography process for isolating γ-T3 with little presence of other tocol isomers from RBODD tocol extract. Peak resolution was best with a load size of about 1% column capacity and a 5-g silica sample cartridge coupled with a 12-g silica column. A binary linear gradient of 0.8% ethyl acetate-acetic acid (99.1:0.9 v/v) to hexane-acetic acid (99.1:0.9 v/v) (50 min) and 100% ethyl acetate-acetic acid (99.1:0.9 v/v) (5 min) gave a fraction (F) with 96.5% γ-T3, which contained 69.3 mg/g. The purity of γ-T3 using these conditions was better than the fraction (E) obtained using 100% hexane/ ethyl acetate-acetic acid (97.3:1.8:0.9 v/v) (50 min) and 100% ethyl acetate (5 min), which contained 47.0% γ-T3.

Example 3

In Example 3, three pretreatments were compared prior to conducting flash chromatography of Example 2, namely 1) applying crude RBODD (Table 7); 2) applying RBODD following acetonitrile extraction, cold step, and solvent evaporation (Table 8); and 3) applying RBODD following acetonitrile extraction, cold step, solvent evaporation, saponification, ether fractionation, and solvent evaporation (Table 9). In this study a different lot of RBODD was used which contained delta tocotrienol. As illustrated, sufficient purification of the tocols cannot be obtained by applying the crude RBODD. Using the abbreviated pretreatment 2 above, i.e., acetonitrile extraction, cold step, and solvent evaporation, 89% purity fractions of gamma tocotrienol (yield=1.3%) can be obtained. Use of the purified tocol concentrate from pretreatment 3 above works best (based upon higher yields) resulting in 100% purity fractions of gamma tocotrienol (yield=10.6%), delta tocopherol (yield=4.7%), and delta tocotrienol (yield=3.0%); however, pretreatment two involves only three steps prior to flash chromatography compared with six steps for pretreatment three. Pretreatment two is commercially faster and less cumbersome, and avoids the use of a toxic solvent (ether) and caustic alkaline reagent (50% potassium hydroxide) required for pretreatment three.

TABLE 7

Crude RBODD directly subjected to Flash Chromatography

| Product | Fraction | Purity (mg tocols/100 mg fraction) | | | | | | | | Total mg tocols in fraction | Yield ((mg tocol/mg starting material) * 100) |
|---|---|---|---|---|---|---|---|---|---|---|---|
| | | αT | αT3 | βT | γT | γT3 | δT | δT3 | Total | | |
| Crude RBODD | 1 | 1.3 | 0.0 | 0.0 | 0.0 | 0.1 | 0.0 | 0.0 | 1.4 | 0.2 | 0.1 |
| Crude RBODD | 2 | 1.9 | 0.0 | 0.0 | 0.0 | 0.0 | 0.0 | 0.0 | 1.9 | 0.1 | 0.0 |
| Crude RBODD | 3 | 0.4 | 1.8 | 0.0 | 0.0 | 0.0 | 0.0 | 0.0 | 2.4 | 0.2 | 0.1 |
| Crude RBODD | 4 | 0.8 | 5.0 | 0.0 | 0.4 | 0.0 | 0.0 | 0.0 | 6.2 | 0.6 | 0.2 |
| Crude RBODD | 5 | 0.0 | 0.0 | 2.0 | 3.7 | 0.0 | 0.0 | 0.0 | 5.8 | 0.4 | 0.1 |
| Crude RBODD | 6 | 0.0 | 0.0 | 0.3 | 6.8 | 0.0 | 0.0 | 0.0 | 7.1 | 0.5 | 0.2 |
| Crude RBODD | 7 | 0.0 | 0.0 | 1.1 | 17.3 | 0.0 | 0.0 | 0.0 | 18.3 | 1.0 | 0.3 |
| Crude RBODD | 8 | 0.0 | 0.0 | 0.0 | 13.7 | 0.0 | 0.0 | 0.0 | 13.7 | 0.9 | 0.3 |
| Crude RBODD | 9 | 0.0 | 0.0 | 0.0 | 8.6 | 0.0 | 0.0 | 0.0 | 8.6 | 0.6 | 0.2 |
| Crude RBODD | 10 | 0.0 | 0.0 | 0.0 | 2.1 | 0.0 | 0.0 | 0.0 | 2.1 | 0.2 | 0.1 |
| Crude RBODD | 11 | 0.0 | 0.0 | 0.0 | 0.0 | 18.5 | 0.0 | 0.0 | 18.5 | 1.4 | 0.5 |
| Crude RBODD | 12 | 0.0 | 0.0 | 0.0 | 0.0 | 33.8 | 0.0 | 0.0 | 33.8 | 1.5 | 0.5 |
| Crude RBODD | 13 | 0.0 | 0.0 | 0.0 | 0.0 | 76.5 | 0.0 | 0.0 | 76.5 | 1.2 | 0.4 |
| Crude RBODD | 14 | 0.0 | 0.0 | 0.0 | 0.0 | 7.2 | 0.3 | 0.0 | 7.4 | 0.2 | 0.1 |
| Crude RBODD | 15 | 0.0 | 0.0 | 0.0 | 0.0 | 0.0 | 2.9 | 0.0 | 2.9 | 0.1 | 0.0 |

TABLE 8

Crude RBODD extracted with acetonitrile, followed by cold step (4 C./24 hr) and subjected to Flash Chromatography.

| Product | Fraction | Purity (mg tocols/100 mg fraction) | | | | | | | | Total mg tocols in fraction | Yield ((mg tocol/mg starting material) * 100) |
| --- | --- | --- | --- | --- | --- | --- | --- | --- | --- | --- | --- |
| | | αT | αT3 | βT | γT | γT3 | δT | δT3 | Total | | |
| RBODD-cold step | 1 | 0.4 | 0.2 | 0.0 | 0.0 | 0.0 | 0.0 | 0.0 | 0.6 | 0.2 | 0.1 |
| RBODD-cold step | 2 | 1.2 | 0.2 | 0.0 | 0.0 | 0.0 | 0.0 | 0.0 | 1.3 | 0.2 | 0.1 |
| RBODD-cold step | 3 | 1.7 | 0.0 | 0.0 | 0.0 | 0.0 | 0.0 | 0.0 | 1.7 | 0.2 | 0.1 |
| RBODD-cold step | 4 | 5.0 | 0.2 | 0.0 | 0.0 | 0.0 | 0.0 | 0.0 | 5.2 | 0.3 | 0.1 |
| RBODD-cold step | 5 | 3.6 | 0.5 | 0.0 | 0.0 | 0.0 | 0.0 | 0.0 | 4.1 | 0.0 | 0.0 |
| RBODD-cold step | 6 | 1.3 | 13.5 | 0.4 | 0.5 | 0.0 | 0.0 | 0.0 | 15.7 | 0.3 | 0.1 |
| RBODD-cold step | 7 | 0.0 | 5.1 | 2.6 | 0.0 | 0.0 | 0.0 | 0.0 | 7.7 | 0.1 | 0.0 |
| RBODD-cold step | 8 | 0.0 | 0.0 | 23.4 | 1.0 | 0.0 | 0.0 | 0.0 | 24.3 | 0.7 | 0.3 |
| RBODD-cold step | 9 | 0.0 | 0.0 | 6.1 | 37.1 | 0.0 | 0.0 | 0.0 | 43.2 | 1.3 | 0.7 |
| RBODD-cold step | 10 | 0.0 | 0.0 | 0.9 | 68.2 | 0.0 | 0.0 | 0.0 | 69.0 | 1.4 | 0.7 |
| RBODD-cold step | 11 | 0.0 | 0.0 | 0.0 | 0.8 | 19.2 | 0.0 | 0.0 | 20.1 | 0.2 | 0.1 |
| RBODD-cold step | 12 | 0.0 | 0.0 | 0.0 | 0.7 | 88.1 | 0.0 | 0.0 | 88.8 | 1.0 | 0.5 |
| RBODD-cold step | 13 | 0.0 | 0.0 | 0.0 | 0.0 | 48.0 | 0.0 | 0.0 | 48.0 | 0.4 | 0.2 |
| RBODD-cold step | 14 | 0.0 | 0.0 | 0.0 | 0.0 | 66.4 | 0.0 | 0.0 | 66.4 | 0.8 | 0.4 |
| RBODD-cold step | 15 | 0.0 | 0.0 | 0.0 | 0.7 | 88.1 | 0.0 | 0.0 | 88.8 | 1.7 | 0.8 |
| RBODD-cold step | 16 | 0.0 | 0.0 | 0.0 | 0.0 | 0.0 | 34.9 | 0.0 | 34.9 | 0.6 | 0.3 |
| RBODD-cold step | 17 | 0.0 | 0.0 | 0.0 | 0.0 | 0.0 | 50.7 | 0.0 | 50.7 | 1.0 | 0.5 |
| RBODD-cold step | 18 | 0.0 | 0.0 | 0.0 | 0.0 | 0.0 | 0.0 | 26.8 | 26.8 | 0.5 | 0.3 |

TABLE 9

Purified RBODD subjected to Flash Chromatography.

| Product | Fraction | Purity (mg tocols/100 mg fraction) | | | | | | | | Total mg tocols in fraction | Yield ((mg tocol/mg starting material) * 100) |
| --- | --- | --- | --- | --- | --- | --- | --- | --- | --- | --- | --- |
| | | αT | αT3 | βT | γT | γT3 | δT | δT3 | Total | | |
| Purified | 1 | 9.0 | 0.0 | 0.0 | 0.0 | 0.0 | 0.0 | 0.0 | 9.0 | 0.5 | 0.6 |
| Purified | 2 | 26.3 | 0.0 | 0.0 | 0.0 | 0.0 | 0.0 | 0.0 | 26.3 | 0.9 | 1.3 |
| Purified | 3 | 6.3 | 17.8 | 0.0 | 0.0 | 0.0 | 0.0 | 0.0 | 24.1 | 1.4 | 1.9 |
| Purified | 4 | 22.2 | 29.0 | 3.2 | 0.0 | 0.0 | 0.0 | 0.0 | 54.5 | 1.5 | 2.0 |
| Purified | 5 | 0.0 | 0.0 | 0.0 | 81.9 | 0.0 | 0.0 | 0.0 | 81.9 | 1.6 | 2.2 |
| Purified | 6 | 0.0 | 0.0 | 0.0 | 10.2 | 75.8 | 0.0 | 0.0 | 86.0 | 1.9 | 2.5 |
| Purified | 7 | 0.0 | 0.0 | 0.0 | 1.4 | 99.0 | 0.0 | 0.0 | 100.4 | 4.1 | 5.5 |
| Purified | 8 | 0.0 | 0.0 | 0.0 | 0.0 | 115.4 | 0.0 | 0.0 | 115.4 | 3.8 | 5.1 |
| Purified | 9 | 0.0 | 0.0 | 0.0 | 0.0 | 2.0 | 98.5 | 0.0 | 100.5 | 3.5 | 4.7 |
| Purified | 10 | 0.0 | 0.0 | 0.0 | 0.0 | 0.0 | 48.6 | 0.0 | 48.6 | 1.2 | 1.6 |
| Purified | 11 | 0.0 | 0.0 | 0.0 | 0.0 | 0.0 | 76.1 | 0.0 | 76.1 | 1.1 | 1.5 |
| Purified | 12 | 0.0 | 0.0 | 0.0 | 0.0 | 0.0 | 0.0 | 101.9 | 101.9 | 1.3 | 1.8 |
| Purified | 13 | 0.0 | 0.0 | 0.0 | 0.0 | 0.0 | 0.0 | 100.7 | 100.7 | 0.9 | 1.2 |

Whereas, the compositions and processes have been described in relation to the drawings and claims, it should be understood that other and further modifications, apart from those shown or suggested herein, may be made within the scope of this invention.

What is claimed is:

1. A process of producing a gamma- and/or delta-tocotrienol-rich fraction from a tocol-rich oil, said process comprising the steps of:
    distilling said tocol-rich oil to produce a tocol concentrate; and
    purifying said tocol concentrate using flash chromatography with a binary mobile phase gradient comprising hexane-acetic acid (99.1:0.9 v/v) and ethyl acetate-acetic acid (99.1:0.9 v/v) for between about 50 minutes and about 55 minutes to produce said gamma- and/or delta-tocotrienol-rich fraction.

2. The process of claim 1 wherein said gamma- and/or delta-tocotrienol-rich fraction is a d-γ-tocotrienol-rich fraction, a δ-tocotrienol-rich fraction or mixture thereof.

3. The process of claim 2 wherein said d-γ-tocotrienol-rich fraction and/or a δ-tocotrienol-rich fraction is substantially free from α-tocols.

4. The process of claim 1 wherein said gamma- and/or delta-tocotrienol-rich fraction comprises about 95% total tocols.

5. The process of claim 4 wherein said gamma-tocotrienol-rich fraction has a yield of approximately 10% and a purity in excess of approximately 95%.

6. The process of claim 4 wherein said delta-tocotrienol-rich fraction has a yield of approximately 3% and a purity in excess of approximately 95%.

7. The process of claim 1 wherein said tocol concentrate contains between about 20% and 50% total tocols.

8. The process of claim 1 wherein said tocol-rich oil is rice bran oil or palm oil.

9. A process of producing a d-γ-tocotrienol and/or δ-tocotrienol extract from a tocol-rich concentrate, said process comprising the steps of:

producing said d-γ-tocotrienol and/or δ-tocotrienol extract from said tocol-rich concentrate using flash chromatography with a binary mobile phase gradient comprising 0.8% ethyl acetate-acetic acid (99.1:0.9 v/v) to hexane-acetic acid (99.1:0.9 v/v) for about 50 minutes and 100% ethyl acetate-acetic acid (99.1:0.9 v/v) for about 5 minutes.

10. The process of claim 9 wherein said d-γ-tocotrienol extract is substantially free from α-tocols.

11. The process of claim 9 wherein said δ-tocotrienol extract is substantially free from α-tocols.

12. The process of claim 9 wherein said d-γ-tocotrienol and/or δ-tocotrienol extract comprises about 95% total tocols.

13. The process of claim 12 wherein said d-γ-tocotrienol extract has a yield of approximately 10% and purity in excess of approximately 95%.

14. The process of claim 12 wherein said δ-tocotrienol extract has a yield of approximately 3% and purity in excess of approximately 95%.

15. The process of claim 9 wherein said tocol-rich concentrate contains between about 20% and 50% total tocols.

16. The process of claim 15 wherein said tocol-rich concentrate is obtained by distillation of a rice bran oil or palm oil.

17. A process, comprising the steps of:
using flash chromatography with a binary mobile phase gradient comprising 0.8% ethyl acetate-acetic acid (99.1:0.9 v/v) to hexane-acetic acid (99.1:0.9 v/v) for about 50 minutes and 100% ethyl acetate-acetic acid (99.1:0.9 v/v) for about 5 minutes to produce a gamma- and/or delta-tocotrienol-rich fraction from a tocol-rich oil.

18. The process of claim 17 wherein said gamma- and/or delta-tocotrienol-rich fraction is a d-γ-tocotrienol-rich fraction, a δ-tocotrienol-rich fraction or mixture thereof.

19. The process of claim 18 wherein said d-γ-tocotrienol-rich fraction and/or a δ-tocotrienol-rich fraction is substantially free from α-tocols.

20. The process of claim 17 wherein said gamma- and/or delta-tocotrienol-rich fraction comprises about 95% total tocols.

21. The process of claim 20 wherein said gamma-tocotrienol-rich fraction has a yield of approximately 10% and a purity in excess of approximately 95%.

22. The process of claim 20 wherein said delta-tocotrienol-rich fraction has a yield of approximately 3% and a purity in excess of approximately 95%.

23. The process of claim 17 wherein said tocol-rich oil is rice bran oil or palm oil.

* * * * *